United States Patent
Curulla-Ferre et al.

(10) Patent No.: US 11,607,673 B2
(45) Date of Patent: Mar. 21, 2023

(54) COPPER-IRON-BASED CATALYTIC COMPOSITION COMPRISING ZEOLITES, METHOD FOR PRODUCING SUCH CATALYTIC COMPOSITION AND PROCESS USING SUCH CATALYTIC COMPOSITION FOR THE CONVERSION OF SYNGAS TO HIGHER ALCOHOLS

(71) Applicants: TOTAL SE, Courbevoie (FR); ETH ZURICH, Zurich (CH)

(72) Inventors: Daniel Curulla-Ferre, Uccle (BE); Joseph Stewart, Uccle (BE); Javier Perez-Ramirez, Zürich (CH); Cecilia Mondelli, Zürich (CH); Ho Ting Luk, Zürich (CH)

(73) Assignees: TOTAL SE, Courbevoie (FR); ETH ZURICH, Zurich (CH)

( * ) Notice: Subject to any disclaimer, the term of this patent is extended or adjusted under 35 U.S.C. 154(b) by 0 days.

(21) Appl. No.: 17/425,932

(22) PCT Filed: Jan. 28, 2020

(86) PCT No.: PCT/EP2020/052026
§ 371 (c)(1),
(2) Date: Jul. 26, 2021

(87) PCT Pub. No.: WO2020/157057
PCT Pub. Date: Aug. 6, 2020

(65) Prior Publication Data
US 2022/0040678 A1 Feb. 10, 2022

(30) Foreign Application Priority Data
Feb. 1, 2019 (EP) .................................... 19305121

(51) Int. Cl.
*B01J 23/78* (2006.01)
*B01J 6/00* (2006.01)
(Continued)

(52) U.S. Cl.
CPC ............... *B01J 23/78* (2013.01); *B01J 6/001* (2013.01); *B01J 23/72* (2013.01); *B01J 23/745* (2013.01);
(Continued)

(58) Field of Classification Search
CPC ........... B01J 23/78; B01J 6/001; B01J 23/72; B01J 23/745; B01J 29/46
(Continued)

(56) References Cited

U.S. PATENT DOCUMENTS 4,595,702 A 6/1986 Chu et al.
5,198,592 A * 3/1993 van Beijnum ......... B01J 23/745
564/485

(Continued)

FOREIGN PATENT DOCUMENTS

EP 2257366 B1 7/2011

OTHER PUBLICATIONS

Ho Ting Luk et al, "Role of Carbonaceous Supports and Potassium Promoter on Higher Alcohols Synthesis over Copper-Iron Catalysts", ACS Catalysis, US, (Sep. 5, 2018), vol. 8, No. 10, 13 pages.
(Continued)

*Primary Examiner* — Douglas B Call
(74) *Attorney, Agent, or Firm* — Ewing & Jones, PLLC

(57) ABSTRACT

The present disclosure relates to a catalyst composition comprising copper and iron on a support for use in a process for the synthesis of higher alcohols from a syngas feed stream comprising hydrogen and carbon monoxide, the catalyst composition being remarkable in that the support is one or more zeolite, in that the total content of iron and
(Continued)

copper is ranging from 1 to 10 wt. % based on the total weight of the catalyst composition and as determined by inductively coupled plasma optical emission spectroscopy, in that the Cu/Fe bulk molar ratio is ranging from 1.1:1.0 to 5.0:1.0 as determined by XRF spectroscopy.

13 Claims, 8 Drawing Sheets

(51) Int. Cl.
| | | |
|---|---|---|
| *B01J 23/72* | (2006.01) | |
| *B01J 23/745* | (2006.01) | |
| *B01J 29/46* | (2006.01) | |
| *B01J 35/02* | (2006.01) | |
| *B01J 35/10* | (2006.01) | |
| *B01J 37/02* | (2006.01) | |
| *C07C 29/156* | (2006.01) | |

(52) U.S. Cl.
 CPC ............ *B01J 29/46* (2013.01); *B01J 35/023* (2013.01); *B01J 35/1014* (2013.01); *B01J 35/1019* (2013.01); *B01J 35/1023* (2013.01); *B01J 37/0201* (2013.01); *C07C 29/156* (2013.01)

(58) Field of Classification Search
 USPC ......................................................... 502/244
 See application file for complete search history.

(56) References Cited

U.S. PATENT DOCUMENTS

| | | | |
|---|---|---|---|
| 7,279,138 B2 | 10/2007 | Pagani et al. | |
| 2003/0158272 A1* | 8/2003 | Davis ..................... | C10G 2/332 518/719 |
| 2006/0088469 A1 | 4/2006 | Perez-Ramirez | |
| 2011/0039954 A1* | 2/2011 | Hu ............................ | B01J 8/26 502/329 |
| 2013/0030224 A1* | 1/2013 | Kim ...................... | B01J 23/8926 568/885 |
| 2013/0324761 A1* | 12/2013 | Hutchings ................ | B01J 29/03 562/549 |
| 2014/0287911 A1* | 9/2014 | Wang ..................... | C01B 3/047 502/244 |
| 2014/0316177 A1* | 10/2014 | Ge ........................ | B01J 29/7007 502/79 |
| 2016/0001267 A1* | 1/2016 | Duvenhage .............. | B01J 23/20 502/336 |
| 2017/0209852 A1 | 7/2017 | Duvenhage et al. | |
| 2018/0221858 A1* | 8/2018 | Hinokuma ................ | C01B 3/04 |

OTHER PUBLICATIONS

Wa Gao et al., "Catalytic Conversion of Syngas to Mixed Alcohols over CuFe-based Catalysts Derived from Layered Double Hydroxides", Catal. Sci. Technol., (2013), vol. 3, 9 pages.

Run Xu et al., "Fe-modified CuMnZrO2 Catalysts for Higher Alcohols Synthesis from Syngas", Journal of Molecular Catalysis A: Chemical, (2004), vol. 221, pp. 51-58.

M. Lin et al., "CO Hydrogenation to Mixed Alcohols over Co-precipitated Cu—Fe Catalysts", Catal. Commun., (2008), vol. 9, pp. 1869-1873.

Mingyue Ding et al., "Effect of Iron Promoter on Structure and Performance of CuMnZnO catalyst for Higher Alcohol Synthesis", Applied Energy, (2012), vol. 97, pp. 543-547.

Mingyue Ding et al., "Design of Bimodal Pore Cu—Fe Based Catalyst with Enhanced Performances for Higher Mcohols Synthesis", Energy Procedia, (2015), vol. 75, pp. 767-772.

Yongwu Lu et al., "High Selectivity Higher Alcohols Synthesis from Syngas over Three-Dimensionally Ordered Macroporous Cu—Fe Catalysts'" Chem Cat Chem, (2014), vol. 6, pp. 473-478.

Hung, "Zeolite ZSM-5 Supported Bimetallic Fe-Based Catalysts for Selective Catalytic Reduction of NO: Effects of Acidity and Metal Loading", Advanced Porous Materials, (2016), vol. 4, pp. 189-199.

International Search Report issued in Application No. PCT/EP2020/052026, dated Apr. 14, 2020; 4 pages.

\* cited by examiner

COPPER-IRON-BASED CATALYTIC COMPOSITION COMPRISING ZEOLITES, METHOD FOR PRODUCING SUCH CATALYTIC COMPOSITION AND PROCESS USING SUCH CATALYTIC COMPOSITION FOR THE CONVERSION OF SYNGAS TO HIGHER ALCOHOLS

CROSS-REFERENCE TO RELATED APPLICATIONS

This application claims the benefit of PCT/EP2020/052026 filed Jan. 28, 2020, which claims priority from EP 19305121.6 filed Feb. 1, 2019, which are incorporated herein by reference in their entireties for all purposes.

FIELD OF THE DISCLOSURE

The present disclosure relates to a copper-iron based catalytic composition comprising zeolites and to a process for converting syngas to higher alcohols using such composition. The present disclosure also relates to a method for producing such catalytic composition.

BACKGROUND OF THE DISCLOSURE

Syngas conversion is well known for producing a variety of chemicals including methanol, alkenes, alkanes. Such products are produced commercially as the methanol synthesis process or the Fischer-Tropsch synthesis (FTS) process. Higher alcohols (C2+) are important compounds with widespread applications in the chemical, pharmaceutical and energy sectors, for instance in the manufacture of pharmaceuticals, detergents, and polymers as well as alternative fuels, gasoline additive and hydrogen carriers. Currently, they are mainly produced by sugar fermentation (ethanol and isobutanol) or hydration of petroleum-derived alkenes. There is currently no commercially process for direct synthesis from syngas. Of the higher alcohols synthesis technologies described in the open literature, alcohol products are predominantly primary alcohols.

Work on this subject was initiated in the 1930s, however, has fluctuated with oil prices. In the last decade, interest has increased significantly in line with the rise of shale gas and renewable resources that can generate gaseous feedstocks. To date, no catalytic system reported has performed sufficiently well to justify an industrial implementation. The majority of systems that have been explored are generally bulk metal catalysts. They are normally split into four main classes: rhodium-based, molybdenum-based, modified Fischer-Tropsch and modified methanol synthesis catalysts. The majority of catalytic systems contain high loadings of their active metals, which limits their economic viability. A variety of metal combinations including CuCo, CuFe and CoMo as either bulk or supported metals have been described. Bulk materials are generally generated via coprecipitation, while supported materials have been prepared through wet-impregnation, sol-gel and incipient wetness, amongst others. A number of Rh-based systems exist but their use is limited due to their high price. Of the supported systems, neutral carriers are widely used.

Run Xu et al., in "Fe-modified $CuMnZrO_2$ Catalysts for Higher Alcohols Synthesis from Syngas", Journal of Molecular Catalysis A: Chemical 221 (2004) 51-58, found that the presence of iron resulted in changes in both structural properties and catalytic performance. The copper dispersion increased and the catalyst stabilization was improved. The role of iron was dependent on the method of catalyst preparation.

M. Lin et al. in, "CO Hydrogenation to Mixed Alcohols over Co-precipitated Cu-Fe Catalysts" Catal. Commun. 9 (2008) 1869-1873, observed that zinc works as an electronic/chemical promoter whereas manganese has a structural role and that the two promoters could act synergistically. They claimed the formation of iron carbides as indispensable for the production of higher alcohols. Hence, a catalyst activated under syngas showed better activity and selectivity to higher alcohols than catalysts activated in $H_2$ or CO.

Mingyue Ding et al., in "Effect of Iron Promoter on Structure and Performance of CuMnZnO catalyst for Higher Alcohol Synthesis", Applied Energy 97 (2012) 543-547, investigated the effect of the iron promoter on the microstructures of CuMnZnO catalysts. The characterization results indicated that incorporation of iron in the CuMnZnO catalyst resulted in the increase of BET surface area and the dispersion of catalyst particles. In the high alcohol synthesis (HAS) reaction, the catalytic activity of CO hydrogenation and the selectivity to C2+ alcohols and hydrocarbons presented an increasing trend with the increase in iron concentration.

Wa Gao et al., in "Catalytic Conversion of Syngas to Mixed Alcohols over CuFe-based Catalysts Derived from Layered Double Hydroxides", Catal. Sci. Technol. 3 (2013) 1324-1332, obtained a uniform and highly dispersed CuFe-based catalyst via a calcination-reduction process of a CuFeMg-layered double hydroxide (LDH) precursor. The catalyst exhibited good activity and selectivity towards the catalytic conversion of syngas to mixed alcohols.

Mingyue Ding et al., in "Design of Bimodal Pore Cu—Fe Based Catalyst with Enhanced Performances for Higher Alcohols Synthesis", Energy Procedia 75 (2015) 767-772, found that both the catalytic activity and selectivity to C2+ alcohols of the catalysts supported on bimodal silica presented increasing performance with the gradual decrease of bimodal support pore size.

U.S. Pat. No. 4,595,702 describes the conversion of syngas into liquid hydrocarbons in the C5 to C24 boiling range of gasoline and diesel fuel with a physical mixture of an iron-based catalyst with a small content of ZSM-5, wherein the nitrogen content is low. The conversion to higher alcohols is not described.

Ho Ting Luk et al., in "Role of Carbonaceous Supports and Potassium Promoter on Higher Alcohols Synthesis over Copper-Iron Catalysts", ACS Catal. 8 (2018) 9604-9618, have indicated that the identification of an effective copper-iron catalyst for the direct conversion of synthesis gas into higher alcohols is hindered by the low solubility of Cu in Fe and the limited understanding of structural and electronic descriptors in such multicomponent system. The commercial carbonaceous carriers are shown to produce an efficient material only if they enable control of the size and location of metal species through confinement in adequately-sized channel, with conical carbon nanofibers being more adequate than carbon nanotubes. Promotion by tiny amounts of potassium was instrumental to further increase the size of Fe-particles and enhance their proximity to Cu. The structural features of the produced catalysts maximized the higher alcohols selectivity (47%) and the alkenes fraction among hydrocarbons (50%). An in-depth kinetic analysis over the top performer provided guidelines to optimize temperature, pressure, $H_2$/CO ratio, and residence time, leading to a space-time yield of 0.53 $g_{HAS}g_{cat}^{-1}h^{-1}$. This value was almost twice as high as the known bimodal silica-supported CuFe system and could be maintained for 100 hours on stream. $CO_2$ was generated in the course of the reaction with a selectivity of 18%.

Yongwu Lu et al. in Chem Cat Chem 2014, 6, 473-478 described the production of higher alcohols from syngas over three-dimensionally ordered macroporous Cu—Fe catalysts. The selectivity obtained toward higher alcohols was considered high by the authors.

US 2006/0088469 describes multimetallic zeolites loaded with transition metals for $N_2O$ abatement in tail-gases. The catalyst comprises Fe and another transition metal such as Cu, Co, Ni, Mn, Cr or V. A synergy between Fe and Cu, Co and Co and Cu was observed.

U.S. Pat. No. 4,595,702 describes a process for converting syngas to hydrocarbon fuels in C5-C24. The conversion is obtained with a low nitrogen content iron catalyst mixed with a zeolite.

US 2017/0209852 describes a method for controllably producing a hematite-containing Fischer-Tropsch catalyst by combining an iron nitrate solution with a precipitating agent solution under particular precipitating conditions.

There is still a need for a catalyst and a process of HAS with high selectivity to high alcohols and limited $CO_2$ production.

SUMMARY

It is an object of the disclosure to provide a new process and a new catalyst for HAS from syngas. Another object is to provide a new process and a new catalyst for HAS from syngas allowing improvement in CO conversion to higher alcohols. A further object is to provide a new process and a new catalyst for HAS from syngas allowing improvement in CO conversion together with limited $CO_2$ production. Another object is to provide a new process and a new catalyst for HAS from syngas showing high stability of the catalyst. The present disclosure provides a solution to one or more of the aforementioned needs.

According to a first aspect, the disclosure provides a catalyst composition comprising an active phase comprising copper and iron on a support for use in a process for the synthesis of higher alcohols from a syngas feed stream comprising hydrogen and carbon monoxide, the catalyst composition being remarkable in that the support is one or more zeolites having a Si/Al molar ratio ranging from 10 and 200 as determined by inductively coupled plasma optical emission spectroscopy (ICP-OES), in that the total content of iron and copper is ranging from 1 to 10 wt. % based on the total weight of the catalyst composition and as determined by X-ray fluorescence (XRF) spectroscopy and in that the Cu/Fe bulk molar ratio is ranging from 1.1/1.0 to 5.0/1.0 as determined by X-ray fluorescence (XRF) spectroscopy and wherein said catalyst composition is a reduced catalyst composition; preferably a reduced catalyst composition as determined X-ray diffraction that is devoid of iron oxide.

The inventors have developed a novel catalytic composition for the conversion of syngas to C2+ alcohols. Surprisingly, it was found that a CuFe catalyst used as the active phase in a catalyst composition wherein the CuFe is supported on a zeolite can achieve a conversion of syngas to higher alcohol with a selectivity to C2+ alcohols of at least 35% at a CO conversion rate of 4%. It was found that it was possible to achieve such results with a low metal loading of up to 10 wt. % or less than 10 wt. % based on the total weight of the catalyst composition, for example with a metal loading of less than 6 wt. % based on the total weight of the catalyst composition. In addition, the new catalyst shows high stability and low $CO_2$ production. It was also found that a catalyst composition having a Si/Al ranging from 10 to 200 allows having a better selectivity toward secondary alcohols.

It is noted that Chin-Te Hung et al. in "*Zeolite ZSM-5 Supported Bimetallic Fe-Based Catalysts for Selective Catalytic Reduction of NO: Effects of Acidity and Metal Loading*", Advanced Porous Materials 4 (2016) 189-199, studied the effects of acidity and metal loading on catalytic activity during selective catalytic reduction (SCR) of NO by $NH_3$ over a series of bimetallic Fe-based H-ZSM5 catalysts (MFe-Z; Z=ZSM5 zeolite; Si/Al=25; M=Cr, Co, Cu, Ce, Pr). It was found that in presence of the primary metal (Fe), further incorporation of a secondary metal (M) provokes formation of ultra-strong Lewis acid sites, which are favourable to the Brønsted-Lewis acid synergy during the $NH_3$—SCR. The bimetallic Fe-based M-Z catalysts exhibited superior $NH_3$—SCR performance over a temperature range of 200-450° C. and a desirable NO conversion of 80%, rendering perspective and practical industrial applications for $DeNO_x$. The catalyst composition of the disclosure is different from the catalyst described in this paper in that it contains more copper than iron. Indeed, the described catalyst compositions of said paper contain a Cu/Fe bulk molar ratio of at most 1.0/1.0. Moreover, said catalyst compositions are described and used for another process.

With preference, one or more of the following embodiments can be used to better define the zeolite support of the present disclosure:

The one or more zeolites are selected from MFI, FAU, MOR, FER, BEA, TON, MTT, OFF families, or any mixture thereof. Preferably, the one or more zeolites are selected or comprise one or more zeolites from the MFI family. More preferably, the one or more zeolites are or comprise ZSM-5. For example, at least 75 wt. % of the one or more zeolites based on the total weight of the zeolites comprise one or more zeolites from the MFI family; preferably at least 80 wt. %, more preferably at least 90 wt. %.

The one or more zeolites have a Si/Al molar ratio ranging from 11 to 190 as determined by inductively coupled plasma optical emission spectroscopy (ICP-OES), preferably from 12 and 170, more preferably from 15 to 140.

The one or more zeolites have a density of Brønsted acid sites ranging from 5 µmol $g^{-1}$ to 500 µmol $g^{-1}$ as determined by Fourier transform infrared (FTIR) spectroscopy of adsorbed pyridine, preferably from 50 µmol $g^{-1}$ to 500 µmol $g^{-1}$.

The one or more zeolites comprise at least one 10-membered ring channel and/or at least one 12-membered ring channel.

The one or more zeolites are MFI zeolites and are selected from ZSM-5, silicalite, boralite C, TS-I, or any mixture thereof; preferably from ZSM-5 and silicalite; more preferably from ZSM-5.

The one or more zeolites have mesoporous surface area comprised between 10 $m^2$ $g^{-1}$ and 600 $m^2$ $g^{-1}$ as determined by Brunauer-Emmett-Teller (BET) method, preferably comprised between 250 $m^2$ $g^{-1}$ and 450 $m^2$ $g^{-1}$, more preferably comprised between 300 $m^2$ $g^{-1}$ and 400 $m^2$ $g^{-1}$.

The one or more zeolites have a density of Lewis-acid sites ranging from 4 µmol $g^{-1}$ to 250 µmol $g^{-1}$ as determined by Fourier transform infrared spectroscopy of adsorbed pyridine, preferably from 15 µmol $g^{-1}$ to 150 µmol $g^{-1}$.

The one or more zeolites have a pore volume comprised between 0.15 cm$^3$ g$^{-1}$ and 1.00 cm$^3$ g$^{-1}$, as determined by nitrogen adsorption measurement, preferably between 0.18 cm$^3$ g$^{-1}$ and 0.50 cm$^3$ g$^{-1}$, more preferably between 0.20 cm$^3$ g$^{-1}$ and 0.30 cm$^3$ g$^{-1}$.

The one or more zeolites have a crystal size comprised between 20 nm and 10 µm as determined by Scanning Electron Microscopy (SEM), preferably between 50 nm and 8 µm, more preferably between 70 nm and 5 µm, and most preferably between 100 nm and 2 µm.

The one or more zeolites have Si/Al molar ratio ranging from 10 to 200 as determined by inductively coupled plasma optical emission spectroscopy (ICP-OES). With preference, The one or more zeolites have a Si/Al molar ratio of at least 10, preferably at least 12, and more preferably at least 15.

The one or more zeolites have a Si/Al molar ratio of at most 200, preferably of at most 150, more preferably of at most 145 even more preferably of at most 140.

The one or more zeolites have a Si/Al molar ratio of 15, 40 or 140.

With preference, one or more of the following embodiments can be used to better define the catalyst composition:

The total content of iron and copper is ranging from 1.5 to 9.0 wt. % as based on the total weight of the catalyst composition as determined by X-ray fluorescence spectroscopy, preferably ranging from 2.0 to 8.0 wt. % or from 3.0 to 7.0 wt. %, more preferably from 4.0 to 6.0 wt. %, even more preferably from 4.5 to 5.5 wt. %, most preferably is at most 5.0 wt. %, and even most preferably is below 5.0 wt. %.

The Cu/Fe bulk molar ratio is ranging from 1.2/1.0 to 4.0/1.0, preferably from 1.5/1.0 to 3.0/1.0; more preferably from 1.7/1.0 to 2.5/1.0, most preferably the Cu/Fe bulk molar ratio is 2.0/1.0.

The catalyst composition is a reduced catalyst composition as determined by X-ray diffraction wherein the reduced catalyst composition is devoid of iron oxide wherein iron oxide is Fe$_2$O$_3$; with preference, the reduced catalyst composition that is devoid of iron oxide comprises less than 0.1 wt. % based on the total weight of the reduced catalyst composition of iron oxide; more preferably less than 0.05 wt. %, even more preferably less than 0.01 wt. %.

The catalyst composition comprising a bimetallic catalyst CuFe on a zeolite support presents a porous surface area with a porous volume comprised between 0.15 cm$^3$ g$^{-1}$ and 0.50 cm$^3$ g$^{-1}$, as determined by nitrogen adsorption measurement, preferably between 0.20 cm$^3$ g$^{-1}$ and 0.30 cm$^3$ g$^{-1}$.

The Cu particle size is at least 7 nm as determined from the (111) reflection in an XRD pattern using the Scherrer equation, preferably at least 8 nm, more preferably at least 9 nm, even more preferably at least 10 nm, and most preferably at least 11 nm.

The Cu particle size is at most 35 nm as determined from the (111) reflection in an XRD pattern using the Scherrer equation, preferably at most 30 nm, more preferably at most 25 nm, even more preferably at most 20 nm, most preferably at most 18 nm, and even most preferably at most 16 nm or 13 nm.

The Cu particle size is ranging from 7 to 35 nm as determined from the (111) reflection in an XRD pattern using the Scherrer equation, preferably from 7 to 30 nm, more preferably from 8 to 25 nm, even more preferably from 9 to 18 nm, most preferably from 10 to 16 nm, and even most preferably ranging from 11 to 13 nm.

In a preferred embodiment, the catalyst composition comprises at least one promoter. Preferably, at least one promoter is selected from alkali metal, more preferably at least one promoter comprises potassium, even more preferably at least one promoter is potassium.

Surprisingly, it was found that the potassium-promoted catalyst composition can achieve a conversion of syngas to higher alcohol with a selectivity C2+ alcohols of more than 40% at a CO conversion rate of 4%.

With preference, the bulk molar ratio of at least one promoter to the copper and iron (i.e. the K/Cu+Fe bulk molar ratio) is ranging from 0.001/1 to 0.5/1 as determined by inductively coupled plasma optical emission spectroscopy, preferably from 0.001/1 to 0.4/1, more preferably from 0.001/1 to 0.3/1, even more preferably from 0.001/1 to 0.2/1, most preferably from 0.001/1 to 0.1/1, even most preferably from 0.002/1 to 0.05/1, or preferably from 0.003/1 to 0.03/1, or more preferably from 0.004/1 to 0.02/1 or more preferably from 0.005/1 to 0.01/1 or more preferably from 0.006/1 to 0.009/1.

In a preferred embodiment, the one or more zeolites have a Si/Al molar ratio ranging from 10 to 200 as determined by inductively coupled plasma optical emission spectroscopy (ICP-OES); the catalyst composition comprises at least one promoter selected from alkali metal, and the bulk molar ratio of at least one promoter to the copper and iron is ranging from 0.001/1 to 0.05/1; with preference:

the one or more zeolites are one or more zeolites from the MFI family, and/or the promoter is potassium, and/or the Si/Al molar ratio is ranging from 15 to 140, and/or the Cu particle size is ranging from 10 to 16 nm as determined from the (111) reflection in an XRD pattern using the Scherrer equation.

In a preferred embodiment, the promoter is present as a counter-cation of said one or more zeolites. The one or more zeolites have been ion-exchanged with at least one promoter. This ion-exchanging step is performed before the step of dry impregnation of the one or more zeolites with the iron and copper. In such an embodiment, the one or more zeolites have a Si/Al molar ratio ranging from 10 to 200 as determined by inductively coupled plasma optical emission spectroscopy (ICP-OES); the catalyst composition comprises at least one promoter selected from alkali metal, and the promoter is a counter-cation of said one or more zeolites; said catalyst composition is a reduced catalyst composition; preferably is a reduced catalyst composition as determined X-ray diffraction that is devoid of iron oxide; with preference:

the one or more zeolites are one or more zeolites from the MFI family, and/or the promoter is potassium, and/or the Si/Al molar ratio is ranging from 15 to 140, and/or the Cu particle size is ranging from 10 to 16 nm as determined from the (111) reflection in an XRD pattern using the Scherrer equation.

With preference, the reduced catalyst composition comprises less than 0.1 wt. % based on the total weight of the reduced catalyst composition of iron oxide; preferably less than 0.05 wt. %, more preferably less than 0.01 wt. %, and/or the iron oxide is Fe$_2$O$_3$.

In a preferred embodiment, the one or more zeolites have a Si/Al molar ratio ranging from 10 to 200 as determined by Inductive Coupled Plasma-Optical Emission Spectroscopy (ICP-OES); the catalyst composition is devoid of promoter; and said catalyst composition is a reduced catalyst composition; preferably a reduced catalyst composition as determined X-ray diffraction that is devoid of iron oxide; with preference:
- the one or more zeolites are one or more zeolites from the MFI family, and/or the Si/Al molar ratio is ranging from 15 to 140, and/or
- the Cu particle size is ranging from 8 to 16 nm as determined from the (111) reflection in an XRD pattern using the Scherrer equation.

With preference, the reduced catalyst composition comprises less than 0.1 wt. % based on the total weight of the reduced catalyst composition of iron oxide; preferably less than 0.05 wt. %, more preferably less than 0.01 wt. %, and/or the iron oxide is $Fe_2O_3$.

According to a second aspect, the disclosure provides a method to produce a catalyst composition according to the first aspect remarkable in that it comprises the following steps:
i. Dry impregnation of the copper and iron, and optionally at least one promoter, on the support being one or more zeolites to obtain a catalyst composition;
ii. Optionally calcining the catalyst composition to obtain a calcined catalyst;
iii. Activating the catalyst composition through a reduction to obtain a reduced catalyst composition.

With preference, the reduced catalyst composition comprises less than 0.1 wt. % based on the total weight of the reduced catalyst composition of iron oxide; preferably less than 0.05 wt. %, more preferably less than 0.01 wt. %, and/or wherein the iron oxide is $Fe_2O_3$.

In an embodiment, the disclosure provides a method to produce a catalyst composition according to the first aspect remarkable in that it comprises the following steps:
i. Dry impregnation of the copper and iron, and optionally at least one promoter, on the support being one or more zeolites, wherein the one or more zeolites comprise at least one promoter as the counter cation of the one or more zeolites, to obtain a catalyst composition;
ii. Optionally calcining the catalyst composition to obtain a calcined catalyst;
iii. Activating the catalyst composition through a reduction to obtain a reduced catalyst composition.

With preference, the reduced catalyst composition comprises less than 0.1 wt. % based on the total weight of the reduced catalyst composition of iron oxide; preferably less than 0.05 wt. %, more preferably less than 0.01 wt. %, and/or wherein the iron oxide is $Fe_2O_3$.

Whatever is the embodiment selected, with preference one or more of the following features can be used to further define the inventive method:
- The activation step iii) is performed in diluted $H_2$ at a temperature above 600 K (326.85° C.).
- The activation step iii) is performed by contacting hydrogen gas with the catalyst composition at a temperature comprised between 500 K (226.85° C.) and 700 K (426.85° C.) at a flow rate comprised between 15 $cm^3$ STP $min^{-1}$ and 25 $cm^3$ STP $min^{-1}$.
- The activation step iii) is performed by contacting hydrogen gas with the catalyst composition at a temperature ranging from 500 K (226.85° C.) to 700 K (426.85° C.), preferably ranging from 550 K (276.85° C.) to 650 K (376.85° C.).
- The activation step iii) is performed by contacting hydrogen gas with the catalyst composition is carried out at a flow rate ranging from 15 $cm^3$ STP $min^{-1}$ to 25 $cm^3$ STP $min^{-1}$, preferably from 17 $cm^3$ STP $min^{-1}$ to 23 $cm^3$ STP $min^{-1}$, more preferably at 20 $cm^3$ STP $min^{-1}$.
- The activation step iii) is performed in diluted $H_2$, preferably hydrogen gas is diluted with a noble gas, selected from helium and/or argon.
- The mixture of hydrogen gas and noble gas has a volume ratio $H_2$/noble gas ranging from 5:1 to 15:1 based on the total volume of said mixture, preferably of 10:1.

According to a third aspect, the disclosure provides a process for the synthesis of higher alcohols from a syngas feed stream comprising hydrogen and carbon monoxide, wherein the process comprises the following steps:
a) providing a syngas feed stream comprising hydrogen and carbon monoxide;
b) providing a catalyst composition according to the first aspect;
c) putting the syngas feed stream in contact with the catalyst composition at a reaction pressure ranging from 1 to 10 MPa and a reaction temperature ranging from 443 K (169.85° C.) to 653 K (379.85° C.); and
d) recovering the effluent containing higher alcohols.

With preference, one or more of the following embodiments can be used to better define the inventive process:
- The process is carried out in a gaseous phase.
- The process is carried out in a continuous-flow reactor.
- The syngas feed stream has a molar $H_2$/carbon oxides ratio ranging from 0.5:1 to 12.0:1, preferably ranging from 0.5:1 to 10.0:1, more preferably ranging from 0.5:1 to 8.0:1, even more preferably ranging from 0.5:1 to 6.0:1, most preferably ranging from 0.5:1 to 4.0:1, even most preferably ranging from 0.7:1 to 3.0:1, or preferably ranging from 1.0:1 to 2.5:1, or more preferably ranging from 1.2:1 to 2.2:1, or most preferably is 2.0:1; wherein the carbon oxide comprises CO and/or $CO_2$, preferably a mixture of CO and $CO_2$.
- The syngas feed stream has a molar $H_2$/CO ratio ranging from 0.5:1 to 12.0:1, preferably ranging from 0.5:1 to 10.0:1, more preferably ranging from 0.5:1 to 8.0:1, even more preferably ranging from 0.5:1 to 6.0:1, most preferably ranging from 0.5:1 to 4.0:1, even most preferably ranging from 0.7:1 to 3.0:1, or preferably ranging from 1.0:1 to 2.5:1, or more preferably ranging from 1.2:1 to 2.2:1.
- The syngas feed stream comprises at least 5 mol % of CO based on the total molar content of the syngas feed, preferably at least 15 mol %, more preferably at least 17 mol %, more preferably at least 20 mol %.
- The syngas feed stream comprises at least 20 mol % of $H_2$ based on the total molar content of the syngas feed, preferably at least 25 mol %, more preferably at least 27 mol %, more preferably at least 30 mol %.
- The syngas feed stream comprises a mixture of carbon monoxide (CO) and of carbon dioxide ($CO_2$); or the syngas feed stream is devoid of carbon dioxide ($CO_2$).
- The syngas feed stream comprises a mixture of carbon monoxide (CO) and of carbon dioxide ($CO_2$) with the content of $CO_2$ being at most 10 mol % based on the total molar content of the syngas feed, preferably ranging from 0.1 to 10 mol %, more preferably ranging from 0.5 to 8.0 mol %, even more preferably ranging from 1.0 to 6 mol %, and most preferably ranging from 3.0 to 5.0 mol %.
- The syngas feed stream further comprises a noble gas, preferably argon. With preference, the molar ratio of $H_2$/Ar is comprised between 4 and 8, preferably between 5 and 7, more preferably, the molar ratio of $H_2$/Ar is equal to 6.

The process is carried out during more than 100 hours without replacement or reactivation of the catalyst, preferably more than 500 hours.

With preference, one or more of the following features can be used to further define the step c) of the inventive process:

The step c) is conducted at a weight hourly space velocity (WHSV) of at least 500 cm$^3$ $g_{cat}^{-1}$ h$^{-1}$, preferably at least 1,000 cm$^3$ $g_{cat}^{-1}$ h$^{-1}$, more preferably of at least 2,000 cm$^3$ $g_{cat}^{-1}$ h$^{-1}$, even more preferably at least 4,000 cm$^3$ $g_{cat}^{-1}$ h$^{-1}$, most preferably at least 6,000 cm$^3$ $g_{cat}^{-1}$ h$^{-1}$, and even most preferably at least 8,000 cm$^3$ $g_{cat}^{-1}$ h$^{-1}$.

The step c) is conducted at a weight hourly space velocity (WHSV) ranging from 500 cm$^3$ $g_{cat}^{-1}$ h$^{-1}$ to 48000 cm$^3$ $g_{cat}^{-1}$ h$^{-1}$, preferably from 6000 cm$^3$ $g_{cat}^{-1}$ h$^{-1}$ to 34000 cm$^3$ $g_{cat}^{-1}$ h$^{-1}$, more preferably from 8000 cm$^3$ $g_{cat}^{1}$ h$^{-1}$ to 32000 cm$^3$ $g_{cat}^{-1}$ h$^{-1}$; even more preferably from 14000 cm$^3$ $g_{cat}^{-1}$ h$^{-1}$ to 28000 cm$^3$ $g_{cat}^{-1}$ h$^{-1}$, most preferably from 16000 cm$^3$ $g_{cat}^{-1}$ h$^{-1}$ to 24000 cm$^3$ $g_{cat}^{-1}$ h$^{-1}$.

The step c) is conducted at a reaction temperature ranging from 493 K (219.85° C.) to 553 (279.85° C.), preferably from 513 K (239.85° C.) to 548 K (274.85° C.), and more preferably at a reaction temperature of 543 K (269.85° C.).

The step c) is conducted at a reaction pressure is ranging from 2 to 9 MPa, preferably from 3 to 7 MPa, more preferably from 4 to 6 MPa, and even more preferably at a reaction pressure of 5 MPa.

According to a fourth aspect, the disclosure provides the use of a catalyst composition comprising an active phase comprising copper and iron on a support in a process for the synthesis of higher alcohols from syngas, the use being remarkable in that the catalyst composition is according to the first aspect.

DETAILED DESCRIPTION

Figure 1:
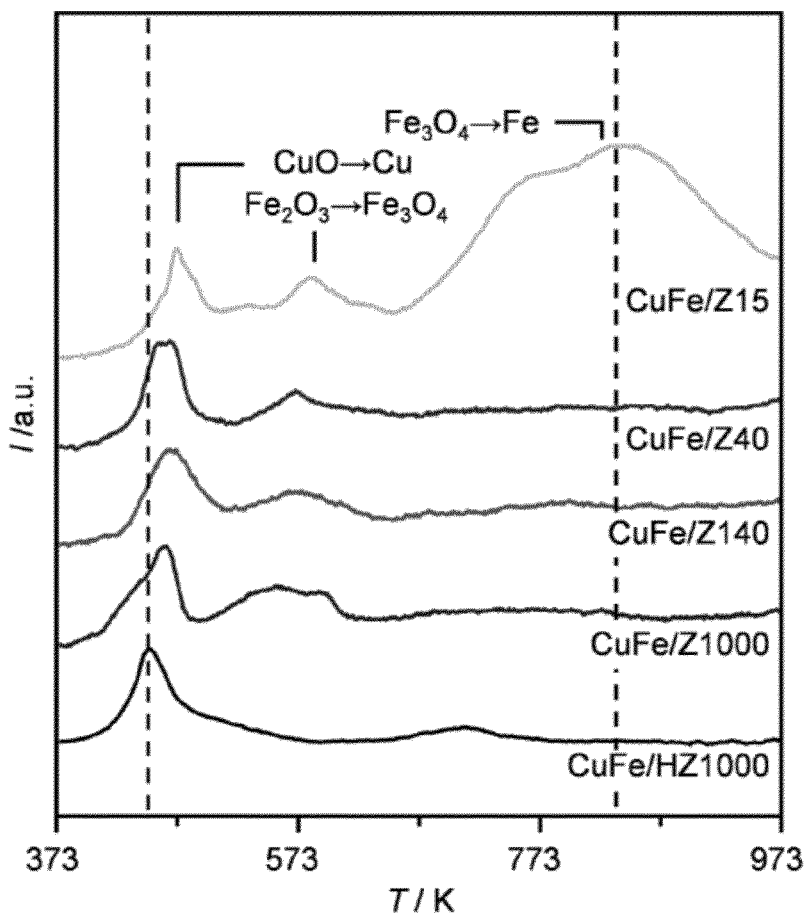
FIG. 1 shows the H$_2$-TPR profiles of the calcined catalyst composition of the present disclosure.

For the purpose of the disclosure, the following definitions are given:

As used herein, the terms "catalyst composition" refer to a composition comprising a main active phase on a support, and an optional alkali promoter. The term catalyst may refer to both a "bulk catalyst" and a "supported catalyst". A bulk catalyst is a catalyst comprising copper and iron. A supported catalyst comprises or consists of the bulk catalyst (i.e. the Cu—Fe catalyst and optional promoter) and a support. The metals Cu—Fe are the main active phase, i.e. the active phase, of the supported catalyst.

The terms "alkane" or "alkanes" as used herein describe acyclic branched or unbranched hydrocarbons having the general formula $C_nH_{2n+2}$, and therefore consisting entirely of hydrogen atoms and saturated carbon atoms; see e.g. IUPAC. Compendium of Chemical Terminology, 2nd ed. (1997). The term "alkanes" accordingly describes unbranched alkanes ("normal-paraffins" or "n-paraffins" or "n-alkanes" or "paraffins") and branched alkanes ("iso-paraffins" or "iso-alkanes") but excludes naphthenes (cycloalkanes). They are sometimes referred to by the symbol "HC—".

The terms "olefin" or "alkene" as used herein relate to an unsaturated hydrocarbon compound containing at least one carbon-carbon double bond. They are sometimes referred to by the symbol "HC═".

The term "hydrocarbon" refers to the alkanes (saturated hydrocarbons) and the alkenes (unsaturated hydrocarbons) together.

As used herein, the terms "C #alcohols", "C #alkenes", or "C #hydrocarbons", wherein "#" is a positive integer, is meant to describe respectively all alcohols, alkenes or hydrocarbons having #carbon atoms. Moreover, the term "C #+ alcohols", "C #+ alkenes", or "C #+ hydrocarbons", is meant to describe all alcohol molecules, alkene molecules or hydrocarbons molecules having #or more carbon atoms. Accordingly, the expression "C5+ alcohols" is meant to describe a mixture of alcohols having 5 or more carbon atoms.

As used herein the terms "higher alcohols", or the term "HA", refer to alcohols containing at least two carbon atoms, such as ethanol, n-propanol; isopropanol; $C_4$-$C_{20}$ alcohols; C2+ alcohols; etc. Both linear and branched alcohols are included when using the term "HA".

The term "1-HA" refers to primary higher alcohols and the term "2-HA" refers to secondary higher alcohols.

In the HAS process according to the disclosure, a syngas feed stream comprising hydrogen (H$_2$) and carbon oxides (CO alone or a mixture of CO and CO$_2$ gases) is caused to interact with a Cu—Fe-based catalyst composition.

Weight hourly space velocity (WHSV) is defined as the volume of feed flowing per unit weight of the catalyst per hour (cm$^3$ g$_{cat}^{-1}$ h$^{-1}$).

The Si/Al molar ratio (silicon to aluminium molar ratio) of one or more zeolites refers to the silicon to aluminium bulk molar ratio of said one or more zeolites. Si/Al molar ratio is determined by inductively coupled plasma optical emission spectroscopy (ICP-OES).

The MFI zeolites are referenced into the following description by "Zx", wherein x represents the Si/Al molar ratio of the zeolite. For instance, Z15 represents an MFI zeolite having a Si/Al molar ratio of 15.

As used herein, the term "HZx" refers to a hierarchical MFI zeolite, having a Si/Al molar ratio of x.

As further used herein, the term "KZx" refers to an MFI zeolite, having a Si/Al molar ratio of x, and being potassium exchanged.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all integer numbers and, where appropriate, fractions subsumed within that range (e.g. 1 to 5 can include 1, 2, 3, 4 when referring to, for example, a number of elements, and can also include 1.5, 2, 2.75 and 3.80, when referring to, for example, measurements). The recitation of endpoints also includes the recited endpoint values themselves (e.g. from 1.0 to 5.0 includes both 1.0 and 5.0). Any numerical range recited herein is intended to include all sub-ranges subsumed therein.

The particular features, structures, characteristics or embodiments may be combined in any suitable manner, as would be apparent to a person skilled in the art from this disclosure, in one or more embodiments.

The Catalyst Composition

The disclosure contemplates the use of a new catalyst composition in a process for the synthesis of higher alcohols from a syngas feed stream comprising hydrogen and carbon monoxide. In accordance with the disclosure, the catalyst composition comprises copper and iron on a support for use in a process for the synthesis of higher alcohols from a syngas feed stream comprising hydrogen and carbon monoxide; the catalyst composition is remarkable in that the support is one or more zeolites, preferably MFI zeolites, in that the total content of iron and copper is ranging from 1 to 10 wt. % based on the total weight of the catalyst composition as determined by X-ray fluorescence (XRF) spectroscopy, in that the Cu/Fe bulk molar ratio is ranging from 1.1/1.0 to 5.0/1.0 as determined by XRF spectroscopy. The support provides mechanical support to the catalyst as well as further enhancing the exposure of the syngas feed stream to the active sites of the catalyst.

With preference, the one or more zeolites are selected from MFI, FAU, MOR, FER, BEA, TON, MTT, OFF families, or any mixture thereof. More preferably, the one or more zeolites are selected from the MFI family. For example, at least 75 wt. % of the one or more zeolites based on the total weight of the zeolites comprise one or more zeolites from the MFI family; preferably at least 80 wt. %, more preferably at least 90 wt. %.

With preference, the one or more zeolites from the MFI family is selected from ZSM-5, silicalite, boralite C, or TS-I. More preferably, the one or more zeolites from the MFI family is selected from ZSM-5 or silicalite.

The zeolite from the FAU family is, preferentially, Y zeolite. The zeolite from the MOR family is, preferentially, mordenite. The zeolite from the FER family is preferably selected from ferrierite, FU-9 or ZSM-35, more preferably is ferrierite. The zeolite from the BEA family is, preferentially, zeolite beta. The zeolite from the TON family is preferably selected from ZSM-22, Theta-1, or NU-10, more preferably is ZSM-22. The zeolite from the MTT family is, preferentially, ZSM-23. The zeolite from the OFF family is, preferentially, offretite It is preferred that the one or more zeolites have a Si/Al molar ratio of at most 200 as determined by inductively coupled plasma optical emission spectroscopy (ICP-OES), preferably of at most 170 or at most 150, more preferably of at most 140 or at most 120, even more preferably of at most 100. In a preferred embodiment, the one or more zeolites have a Si/Al molar ratio ranging between 15 and 200. More precisely, acidic zeolites with a Si/Al molar ratio ranging between 10 and 200 are considered in the context of the disclosure.

In a preferred embodiment, the one or more zeolites have Si/Al molar ratio ranging from 10 to 200 as determined by inductively coupled plasma optical emission spectroscopy (ICP-OES), preferably ranging from 11 to 190; more preferably ranging from 12 to 170 or ranging from 12 to 150; more preferably ranging from 14 to 145, and even more preferably ranging from 15 to 140. In specific examples, the one or more MFI zeolites have a Si/Al molar ratio of 15, 40 or 140. When the catalyst composition comprises one or more zeolites have Si/Al molar ratio ranging from 10 to 200, enhanced selectivity of desired products is achieved with or without a promoter.

Advantageously, the zeolite support presents mesoporous surface area comprised between 10 m$^2$ g$^{-1}$ and 600 m$^2$ g$^{-1}$ as determined by Brunauer-Emmett-Teller (BET) method, preferably comprised between 250 m$^2$ g$^{-1}$ and 450 m$^2$ g$^{-1}$, more preferably comprised between 300 m$^2$ g$^{-1}$ and 400 m$^2$ g$^{-1}$.

The pore volume has been determined by nitrogen adsorption measurement and is ranging between 0.15 cm$^3$g$^{-1}$ and 1.00 cm$^3$ g$^{-1}$, as determined by nitrogen adsorption measurement, preferably between 0.18 cm$^3$ g$^{-1}$ and 0.50 cm$^3$ g$^{-1}$, more preferably between 0.20 cm$^3$ g$^{-1}$ and 0.30 cm$^3$ g$^{-1}$.

Optionally, a desilication step has been performed on the zeolite, in order to introduce mesoporosity to the support. This surface area thus increases to above 500 m$^2$ g$^{-1}$ as determined by the Brunauer-Emmett-Teller (BET) method and the pore volume also increase to above 0.40 cm$^3$g$^{-1}$. The desilication step allows for obtaining a zeolite that is called "hierarchical zeolite".

The density of Brønsted-acid sites ($C_{BAS}$) has been determined by FTIR spectroscopy of adsorbed pyridine. By coherence with the Si/Al molar ratio, acidic zeolite supports with a Si/Al molar ratio ranging between 15 and 500 have a $C_{BAS}$ comprised between 50 µmol/g and 350 µmol and less acidic zeolite supports with a Si/Al molar ratio ranging between 500 and 1500 have a $C_{BAS}$ inferior to 50 µmol/g.

The density of Lewis-acid sites ($C_{LAS}$) has been determined by FTIR spectroscopy of adsorbed pyridine. The trend follows the Si/Al molar ratio and the density of Brønsted-acid sites ($C_{BAS}$) of the zeolite carrier. An acidic zeolite support has a $C_{LAS}$ ranging between 12 µmol g$^{-1}$ and 60 µmol g$^{-1}$ while less acidic zeolite support has a $C_{LAS}$ inferior to 12 µmol g$^{-1}$.

In a preferred embodiment, the one or more zeolites have a crystal size comprised between 20 nm and 10 µm as determined by Scanning Electron Microscopy (SEM), preferably between 50 nm and 8 µm, more preferably between 70 nm and 5 µm, and most preferably between 100 nm and 2 µm.

The Cu—Fe content of the catalyst composition is ranging from 1 to 10 wt. % based on the total weight of the catalyst composition and as determined by X-ray fluorescence spectroscopy. With preference, the Cu—Fe content is ranging from 1.5 to 9.0 wt % or from 2.0 to 8.0 wt. % based on the total weight of the catalyst composition as determined by X-ray fluorescence spectroscopy, preferably ranging from 3.0 to 7.0 wt. %, more preferably from 4.0 to 6.0 wt. %; even more preferably from 4.5 to 5.5 wt. % and most preferably below 5.0 wt. %. In an embodiment, the Cu—Fe content is ranging from 2.0 to 4.9 wt. % based on the total weight of the catalyst composition as determined by X-ray fluorescence spectroscopy.

The Cu/Fe bulk molar ratio of the catalyst composition is ranging from 1.1/1.0 to 5.0/1.0. With preference, the Cu/Fe bulk molar ratio is ranging from 1.2/1.0 to 4.0/1.0, preferably from 1.5/1.0 to 3.0/1.0; more preferably from 1.7/1.0 to 2.5/1.0; most preferably the Cu/Fe bulk molar ratio is 2.0/1.0.

In a preferred embodiment, the Cu particle size is ranging from 7 to 35 nm as determined from the (111) reflection in an XRD pattern using the Scherrer equation, preferably from 7 to 30 nm, more preferably from 8 to 25 nm, even more preferably from 9 to 18 nm, most preferably from 10 to 16 nm, and even most ranging from 11 to 13 nm.

In a preferred embodiment, the catalyst composition further comprises at least one promoter selected from alkali and alkaline earth metal. With preference, at least one promoter is selected from alkali metal, preferably at least one promoter comprises potassium, more preferably at least one promoter is potassium.

The at least one promoter can be ion-exchanged with the zeolite before the introduction of the copper and iron phase and/or can be added to the supported catalyst of copper and iron.

In a preferred embodiment, the bulk molar ratio of at least one promoter to the copper and iron is ranging from 0.001/1 to 0.5/1 as determined by inductively coupled plasma optical emission spectroscopy, preferably from 0.001/1 to 0.4/1, more preferably from 0.001/1 to 0.3/1, even more preferably from 0.001/1 to 0.2/1, most preferably from 0.001/1 to 0.1/1, even most preferably from 0.002/1 to 0.05/1, or preferably from 0.003/1 to 0.03/1, or more preferably from 0.004/1 to 0.02/1 or more preferably from 0.005/1 to 0.01/1 or more preferably from 0.006/1 to 0.009/1.

The catalyst composition is a calcined catalyst composition having a BET surface area in the range of from 20 m$^2$ g$^{-1}$ to 1000 m$^2$ g$^{-1}$ as determined according to N$_2$ sorption analysis, preferably from 100 m$^2$ g$^{-1}$ to 400 m$^2$ g$^{-1}$. With preference, the catalyst composition is a reduced catalyst composition as determined by X-ray diffraction wherein the reduced catalyst composition is devoid of iron oxide. In accordance with the present disclosure, the reduced catalyst composition is devoid of iron oxide means that the reduced catalyst composition comprises less than 0.1 wt. % based on the total weight of the reduced catalyst composition of iron oxide; preferably less than 0.05 wt. %, more preferably less than 0.01 wt. %. In accordance with the present disclosure, the reduced catalyst composition is devoid of iron oxide means that the reduced catalyst composition is devoid of iron oxide being Fe$_2$O$_3$.

In a preferred embodiment, the one or more MFI zeolites have a Si/Al molar ratio ranging from 10 to 200 as determined by inductively coupled plasma optical emission spectroscopy (ICP-OES); the catalyst composition is a reduced catalyst composition and comprises at least one promoter selected from alkali metal, and the bulk molar ratio of at least one promoter to the copper and iron is ranging from 0.001/1 to 0.05/1; with preference, the promoter is potassium and/or the Si/Al molar ratio is ranging from 15 to 140 and/or the Cu particle size is ranging from 10 to 16 nm as determined from the (111) reflection in an XRD pattern using the Scherrer equation. With preference, the catalyst composition is a reduced catalyst composition as determined X-ray diffraction that is devoid of iron oxide. This embodiment allows achieving selectivity of more than 35% at a CO conversion rate of 4% together with a low CO$_2$ selectivity of less than 10%.

In a preferred embodiment, the one or more MFI zeolites have a Si/Al molar ratio ranging from 10 to 200 as determined by inductively coupled plasma optical emission spectroscopy (ICP-OES); the catalyst composition is a reduced catalyst composition and comprises at least one promoter selected from alkali metal, and the promoter is a counter-cation of said one or more MFI zeolites; with preference, the promoter is potassium and/or the Si/Al molar ratio is ranging from 15 to 140 and/or the Cu particle size is ranging from 10 to 16 nm as determined from the (111) reflection in an XRD pattern using the Scherrer equation. With preference, the catalyst composition is a reduced catalyst composition as determined X-ray diffraction that is devoid of iron oxide. This embodiment also allows achieving selectivity of more than 35% at a CO conversion rate of 4% together with a low CO$_2$ selectivity of less than 10%.

In a preferred embodiment, the one or more MFI zeolites have a Si/Al molar ratio ranging from 10 to 200 as determined by inductively coupled plasma optical emission spectroscopy (ICP-OES); the catalyst composition is devoid of promoter and is a reduced catalyst composition; with preference, the Si/Al molar ratio is ranging from 15 to 140 and/or the Cu particle size is ranging from 8 to 16 nm as determined from the (111) reflection in an XRD pattern using the Scherrer equation. With preference, the catalyst composition is a reduced catalyst composition as determined X-ray diffraction that is devoid of iron oxide. This embodiment allows achieving selectivity of more than 30% at a CO conversion rate of 4% together with a low CO$_2$ selectivity of less than 15%.

Method to Prepare the Catalyst Composition

The disclosure also provides a method to produce a catalyst composition according to the first aspect that is remarkable in that it comprises the following steps:

i. Dry impregnation of the copper and iron, and optionally at least one promoter, on the support being one or more zeolites to obtain a catalyst composition;

ii. Optionally calcining the catalyst composition to obtain a calcined catalyst;

iii. Activating the catalyst composition through a reduction to obtain a reduced catalyst composition;

with preference, the activation step iii) is performed in diluted H$_2$ at a temperature above 600 K (326.85° C.).

In an embodiment, the disclosure provides a method to produce a catalyst composition according to the first aspect remarkable in that it comprises the following steps:

i. Dry impregnation of the copper and iron, and optionally at least one promoter, on the support being one or more zeolites, wherein the one or more zeolites comprise at least one promoter as the counter cation of the one or more zeolites, to obtain a catalyst composition;
ii. Optionally calcining the catalyst composition to obtain a calcined catalyst;
iii. Activating the catalyst composition through a reduction to obtain a reduced catalyst composition;

with preference, the activation step iii) is performed in diluted $H_2$ at a temperature above 600 K (326.85° C.).

Whatever is the embodiment selected, step iii) of the process comprises the step of reducing the catalyst composition, in order to activate the catalyst composition for the catalytic conversion of syngas to C2+ alcohols. The reduction can be performed with a flow of hydrogen, preferably mixed with a noble gas, for instance, helium, argon or a mixture thereof. The reduction can be carried out at temperature comprised between 500 K (226.85° C.) and 700 K (426.85° C.), preferably between 550 K (276.85° C.) and 650 K (376.85° C.). The flow rate of the hydrogen can be comprised between 15 cm$^3$ STP min$^{-1}$ and 25 cm$^3$ STP min$^{-1}$, preferably between 17 cm$^3$ STP min$^{-1}$ and 23 cm$^3$ STP min$^{-1}$, more preferably at 20 cm$^3$ STP min$^{-1}$. The hydrogen can be diluted into the noble gas at a volume ratio $H_2$/noble gas ranging between 5% and 15% based on the total volume of said mixture, preferably of 10%.

Whatever is the embodiment selected, the copper and the iron are impregnated under the forms of copper precursors and iron precursors, respectively. Said precursors are nitrate derivatives, chloride derivatives and/or acetate derivatives. Preferentially, said precursors are nitrate derivatives.

The HAS Process

The disclosure provides a process for the synthesis of higher alcohols from a syngas feed stream comprising hydrogen and carbon monoxide, wherein the process comprises the following steps:
a) providing a syngas feed stream comprising hydrogen and carbon monoxide;
b) providing a catalyst composition as described above;
c) putting the syngas feed stream in contact with the catalyst composition at a reaction pressure ranging from 1 to 10 MPa and a reaction temperature ranging from 443 K (169.85° C.) to 653 K (379.85° C.); and
d) recovering the effluent containing higher alcohols.

The process can be carried out in a gaseous phase or in a liquid phase. The solvent that can be used for the reaction in liquid phase includes hydrocarbons and other solvents which are preferably insoluble or sparingly soluble in water. The process can be carried out in a liquid phase or in a gaseous phase. Preferably, the process is carried out in a gaseous phase.

The process is carried out in a reactor comprising:
lines to introduce a syngas as a feed stream to the reactor and to remove the products from the reactor;
a device for heating the reactor;
a temperature sensor and controller to control the reactor temperature to be within the reaction temperature range of 443 K (169.85° C.) to 653 K (379.85° C.);
flow controllers to control the rate of the feed stream to the reactor; and
a pressure controller to control the reactor pressure to be within the reaction pressure range of from 1 to 10 MPa.

Step b) of the process comprises the step of performing a calcination of the catalyst composition. The calcination can be performed in air atmosphere, at a temperature ranging between 400 K (126.85° C.) and 700 K (426.85° C.), preferably ranging between 500 K (226.85° C.) and 600 K (326.85° C.), for instance at 573 K (299.85° C.). The calcination can also be performed for at least 2 hours, preferably for at least 3 hours.

In accordance with the disclosure, the syngas feed stream comprises hydrogen ($H_2$) and carbon oxides (CO alone or a mixture of CO and $CO_2$ gases). With preference, the feed stream comprises hydrogen ($H_2$) and carbon monoxide (CO).

In a preferred embodiment, the syngas feed stream comprises at least 20 mol % of hydrogen ($H_2$) based on the total molar content of the syngas feed, preferably at least 25 mol %, more preferably at least 27 mol %, and more preferably at least 30 mol %.

In an embodiment, the syngas feed stream comprises at most 90 mol % of hydrogen ($H_2$) based on the total molar content of the syngas feed, preferably at most 80 mol %, more preferably at most 70 mol %, and even more preferably at most 60 mol %.

In a preferred embodiment, the syngas feed stream comprises at least 10 mol % of carbon monoxide (CO) based on the total molar content of the syngas feed, preferably at least 15 mol %, more preferably at least 17 mol %, and more preferably at least 20 mol %.

In an embodiment, the syngas feed stream comprises at most 90 mol % of carbon monoxide (CO) based on the total molar content of the syngas feed, preferably at most 80 mol %, more preferably at most 70 mol %, and more preferably at most 60 mol %.

In a preferred embodiment, the syngas feed stream has a molar $H_2$/carbon oxides ratio ranging from 0.5:1 to 12.0:1, preferably ranging from 0.5:1 to 10.0:1, more preferably ranging from 0.5:1 to 8.0:1, even more preferably ranging from 0.5:1 to 6.0:1, most preferably ranging from 0.5:1 to 4.0:1, even most preferably ranging from 0.7:1 to 3.0:1, or preferably ranging from 1.0:1 to 2.5:1, or more preferably ranging from 1.2:1 to 2.2:1; wherein the carbon oxide comprises CO and/or $CO_2$, preferably a mixture of CO and $CO_2$.

The syngas feed stream has a molar $H_2$/CO ratio ranging from 0.5:1 to 12.0:1, preferably ranging from 0.5:1 to 10.0:1, more preferably ranging from 0.5:1 to 8.0:1, even more preferably ranging from 0.5:1 to 6.0:1, most preferably ranging from 0.5:1 to 4.0:1, even most preferably ranging from 0.7:1 to 3.0:1, or preferably ranging from 1.0:1 to 2.5:1, or more preferably ranging from 1.2:1 to 2.2:1.

The syngas feed stream used in the process of the disclosure comprises CO and $H_2$, or $H_2$ and a mixture of CO and $CO_2$. Preferably, the syngas feed stream may also comprise a further gaseous component such as an inert gas. The inert gas is for example argon.

In an embodiment, the syngas feed stream comprises a mixture of carbon monoxide (CO) and of carbon dioxide ($CO_2$) with the content of $CO_2$ being at most 10 wt. % based on the total molar content of the syngas feed, preferably ranging from 0.1 to 10.0 wt. %, more preferably ranging from 0.5 to 8.0 wt. %, even more preferably ranging from 1.0 to 6.0 wt. %, and most preferably ranging from 3.0 to 5.0 wt. %.

The process is carried at a reaction temperature ranging from 443 K (169.85° C.) to 653 K (379.85° C.), and preferably from 493 K (219.85° C.) to 553 K (279.85° C.). The reaction temperature is preferably at least 498 K (224.85° C.), more preferably at least 503 K (229.85° C.), even more preferably at least 508 K (234.85° C.) and most preferably at least 513 K (239.85° C.); and/or the reaction temperature is preferably at most 548 K (274.85° C.). The person skilled in the art may increase the reaction temperature in order to increase the conversion rate of the carbon monoxide.

The higher alcohols are preferably recovered in a gaseous phase and further subjected to a separation treatment. The process is carried at a reaction pressure ranging from 1.0 to 10.0 MPa, preferably ranging from 2.0 to 9.0 MPa, more preferably ranging from 3.0 to 7.0 MPa. The reaction pressure is preferably at least 3.5 MPa, more preferably at least 4.0 MPa; and/or, the reaction pressure is preferably at most 6.5 MPa, more preferably at most 6.0 MPa.

In a preferred embodiment, the step c) of putting the syngas feed stream in contact with the catalyst composition, is conducted at a weight hourly space velocity (WHSV) of at least 1,000 cm$^3$ g$_{cat}^{-1}$ h$^{-1}$ at standard temperature and pressure (STP). The weight hourly space velocity is defined in the volume of reactant gases per hour per weight of catalyst composition charged to the reactor. With preference, the WHSV is of at least 2,000 cm$^3$ g$_{cat}^{-1}$ h$^{-1}$, preferably at least 4,000 cm$^3$ g$_{cat}^{-1}$ h$^{-1}$, more preferably at least 6,000 cm$^3$g$_{cat}^{-1}$ h$^{-1}$, even more preferably at least 8,000 cm$^3$ g$_{cat}^{-1}$ h$^{-1}$; and/or of at most 100,000 cm$^3$ g$_{cat}^{-1}$ h$^{-1}$, preferably at most 50,000 cm$^3$ g$_{cat}^{-1}$ h$^{-1}$, more preferably at most 40,000 cm$^3$ g$_{cat}^{-1}$ h$^{-1}$, even more preferably at most 30,000 cm$^3$ g$_{cat}^{-1}$ h$^{-1}$, or 24000 cm$^3$ g$_{cat}^{-1}$ h$^{-1}$.

Specific reaction inductions include a weight hourly space velocity of 4000 cm$^3$ g$_{cat}^{-1}$ h$^{-1}$, a temperature of 543 K (269.85° C.) and a pressure of 5.0 MPa and a syngas with an H$_2$/CO molar ratio of 2.

It is preferable to dilute syngas with a noble gas, for example, argon.

According to the disclosure, the process can be carried out with stable performance with respect to activity and selectivity for more than 100 hours without replacement or reactivation of the catalyst.

In an embodiment, the process is carried out in a fixed bed or fluidised bed reactor comprising at least one catalytic bed. Such reactors are well-known from the person skilled in the art and for instance described in EP2257366 or in U.S. Pat. No. 7,279,138.

Test and Determination Methods

Inductively coupled plasma optical emission spectroscopy (ICP-OES) has been applied to determine the contents of K, Si and Al in the catalyst composition. To achieve this analytical technique, Horiba Ultra 2 instrument equipped with a photomultiplier tube detector was used.

X-ray fluorescence spectroscopy (XRF) was performed using an Orbis Micro-EDXRF spectrometer equipped with an Rh source operated at 35 kV and 500 μA and a silicon drift detector to obtain the molar Cu/Fe bulk molar ratio and CuFe loading of the supported catalysts.

N$_2$ sorption at 77 K (−196.15° C.) was measured in a Micromeritics TriStar II instrument after degassing the samples at 573 K (299.85° C.) under vacuum for 3 h.

The volume of the pores of the one or more zeolites was determined from the volume measured at the equilibrium between the gas pressure (p) and the saturation pressure (p$_0$).

The surface area of supports and catalysts was calculated by applying the BET method.

Powder X-ray diffraction (XRD) was conducted using a PANalytical X'Pert Pro-MPD diffractometer with Ni-filtered Cu Kα radiation (I=0.1541 nm), acquiring data in the 10-70° 2θ range with an angular step size of 0.033° and a counting time of 8 s per step.

The size of metallic copper crystallites was estimated by using the Scherrer equation. The size and location of metallic copper and iron particles were determined by high-resolution transmission electron microscopy (HRTEM) and scanning transmission electron microscopy coupled to energy-dispersive X-ray spectroscopy (STEM-EDX).

Temperature-programmed reduction with hydrogen (H$_2$-TPR) was carried out using a Micromeritics Autochem 2950 HP unit equipped with a thermal conductivity detector and coupled to a Pfeiffer Vacuum Omnistar™ GSD-320 quadrupole mass spectrometer. 0.050 g of the sample were dried in an Ar flow of 20 cm$^3$ STP min$^{-1}$ at 423 K (149.85° C.) for 1 h and cooled to 323 K (49.85° C.) before the temperature was ramped up to 973 K (699.85° C.) (10 K min$^{-1}$) in a 5 vol % H$_2$/Ar flow of 20 cm$^3$ STP min$^{-1}$ for the analysis.

Fourier transform infrared spectroscopy (FTIR) of adsorbed pyridine was conducted in a Bruker IFS 66 spectrometer. The samples were pressed into self-supporting wafers of ca. 1 cm$^2$ and degassed under vacuum (10$^{-3}$ mbar) at 473 K (199.85° C.) for 4 h, followed by pyridine adsorption at room temperature. Gaseous and weakly adsorbed molecules were removed by evacuation at 473 K (199.85° C.) for 30 min. Spectra were acquired collecting 32 scans in the range of 650-4000 cm$^{-1}$ with a resolution of 4 cm$^{-1}$.

High-resolution transmission electron microscopy (HRTEM) and scanning transmission electron microscopy coupled to energy-dispersive X-ray spectroscopy (STEM-EDX) were conducted in an FEI Talos F200A instrument equipped with a high-brightness field emission gun, a high-angle annular dark-field (HAADF) detector, and a large collection angle EDX detector, operated at 200 kV. Catalyst powders were dispersed on nickel grids coated with a continuous carbon film.

Thermogravimetric analysis (TGA) has been used to check the amount of coke deposition on the used catalyst. TGA was carried out in a Linseis DSC PT1600 instrument. The amount of coke was determined by registering the weight loss curve in the temperature range of 303-1173 K (29.85-899.95° C.) at a rate of 10 K min$^{-1}$ under 25 cm$^3$ STP min$^{-1}$ of airflow.

Gas chromatography experiments were carried out to determine quantitatively the selectivity of the reaction. The gas chromatograph comprised two columns (ShinCarbon ST and PoraPLOT Q PT), a thermal conductivity detector (TCD) and a flame ionization detector (FID) and was operated with the ChemStation software by Agilent.

Scanning Electron Microscopy (SEM) has been used to determine the crystal size of the one or more zeolites The conversion of carbon monoxide (X$_{CO}$) was determined according to formula (1):

$$X_{CO} = \frac{n_{CO,in} - n_{CO,out}}{n_{CO,in}} \cdot 100\% \qquad (1)$$

wherein n$_{CO,in}$ and n$_{CO,out}$ are the molar flows of CO (expressed in mmol h$^{-1}$) at the inlet and outlet of the reactor, respectively.

The selectivity to product i (S$_i$) was calculated using equation (2)

$$S_i = \frac{n_{i,out} N_{c,i}}{\Sigma n_{i,out} N_{c,i}} \cdot 100\% \qquad (2)$$

wherein n$_{i,out}$ and N$_{c,i}$ are the molar flow of product i at the outlet of the reactor and the number of carbon atoms in product i, respectively. The selectivity to C2+ alcohols was obtained summing the individual selectivities to alcohols with 2 or more carbon atoms, while that to hydrocarbons summing the individual selectivities to hydrocarbon with 1 or more carbon atoms.

The space-time yield of HA ($STY_{HA}$) expressed in $g_{HA}$ $g_{cat}^{-1}$ $h^{-1}$ was calculated using equations (3):

$$STY_{HA} = \sum S_{j,HA} MW_{j,HA} \frac{X_{CO} n_{CO,in}}{m_{cat}} \quad (3)$$

wherein $m_{cat}$ is the mass of the catalyst and $MW_{j,HA}$ is the molecular weight of higher alcohols (i.e. C2+ alcohols) containing j carbon atoms.

The carbon balance was determined according to equation (4) and was always higher than 95%.

$$\varepsilon_C = \frac{n_{CO,in} - \Sigma n_{i,out} N_{c,i}}{n_{CO,in}} \cdot 100\% \quad (4)$$

Feeding experiments were conducted by introducing individually methanol, primary alcohols (molar ethanol/propan-1-ol/butan-1-ol/water ratio=1/1/1/2), secondary alcohols (molar propan-2-ol/butan-2-ol/water ratio=1/1/2.5), alkenes, and alkanes (propylene/propane/but-1-ene/butane/water=1/1/1/1/3.5) in the presence of Ar or syngas mixture ($H_2$/CO=2) over Z40. The liquid or gas was introduced at a total concentration of 2% and a space velocity of 8000 $cm^3$ $g_{cat}^{-1}$ $h^{-1}$ to mimic the outlet stream conditions at a conversion level of 4%.

EXAMPLES

The embodiments of the present disclosure will be better understood by looking at the different examples below.

Example 1: Preparation of the MFI Zeolite Supports

Various MFI zeolites were used as supports for CuFe catalysts. Silicalite with a Si/Al molar ratio of 1060 was purchased in protonic form (Tosoh Corporation, HSZ-890/HOA, denoted as Z1000) and was used as received. Hierarchical silicalite (denoted as HZ1000) was prepared by treating Z1000 in aqueous NaOH (Merck-Schuchardt, 99%, 0.2 M, 338 K (64.85° C.), 33.3 $g_{zeolite}$ $dm^{-3}$, 30 min) using an Easymax™ 102 (Mettler Toledo), followed by quenching in an ice-water mixture. The solid was recovered by filtration, washed extensively with water, dried at 338 K (64.85° C.) overnight, and converted into the protonic form by ion exchange in aqueous $NH_4NO_3$ (Acros Organics, >99%, 0.1 M, 298 K (24.85° C.), 10 zeolite $dm^{-3}$, 8 h, 3 cycles), followed by calcination in static air at 823 K (549.85° C.) (ramp rate=5 K $min^{-1}$) for 5 h. MFI zeolites with nominal Si/Al molar ratios of 15, 40, and 140 (Zeolyst Ltd., denoted as Zx, where x is the Si/Al molar ratio) were delivered in ammonium form and calcined as described above, to convert them into the corresponding protonic forms. Z40 samples partially ($KZ40_p$) and fully (KZ40) exchanged with potassium were obtained by three consecutive treatments of the as-received Z40 in aqueous $KNO_3$ (1.0 mM and 0.1 M, respectively, 10 $g_{zeolite}$ $dm^{-3}$, 8 h). The zeolite recovered by filtration after the third treatment was washed with deionized water (1 $dm^3$ $g_{zeolite}^{-1}$), dried, and calcined under the same conditions as for the other samples. Table 1 indicates the data of the MFI zeolites supports used in the present disclosure.

TABLE 1

Characterization data of MFI zeolites with different acidity and porosity used as catalyst supports.

| Supports | $V_{pores}{}^a$ ($cm^3$ $g^{-1}$) | $S_{BET}{}^{b,d}$($m^2$ $g^{-1}$) | $C_{BAS}{}^c$ (µmol $g^{-1}$) | $C_{LAS}{}^c$ (µmol $g^{-1}$) |
|---|---|---|---|---|
| Z15 | 0.27 | 383 | 290 | 39 |
| Z40 | 0.25 | 399 | 176 | 23 |
| Z140 | 0.23 | 369 | 99 | 14 |
| Z1000 | 0.19 | 328 | 19 | 10 |
| KZ40 | 0.24 | 382 | 6 | 9 |
| HZ1000 | 0.45 | 521 | 17 | 30 |

$^a$Volume adsorbed at $p/p_0$ = 0.99; wherein $p/p_0$ is defined as the relative pressure of equilibrium gas pressure (p) to the saturation pressure ($p_0$).
$^b$BET method.
$^c$FTIR of adsorbed pyridine.
$^d$Mesoporous surface area determined by the t-plot method in bracket.

Example 2: Deposition of the Bimetallic CuFe Catalyst on the MFI Zeolite Supports Supported CuFe catalysts with a Cu/Fe bulk molar ratio of 2 and CuFe loading of 5 wt. % were prepared by dry impregnation.

The copper precursor was $Cu(NO_3)_2 \cdot 3H_2O$, and the iron precursor was $Fe(NO_3)_3 \cdot 9H_2O$.

$Cu(NO_3)_2 \cdot 3H_2O$ (0.278 g, Aldrich Fine Chemicals, 98-103%) and $Fe(NO_3)_3 \cdot 9H_2O$ (0.232 g, Aldrich Fine Chemicals, >98%) were dissolved in an amount of deionized water equal to the pore volume of the support and added drop-wise to the support (2.00 g, except KZ40p) under magnetic stirring. The resulting solid was kept under stirring for 30 min, dried in air at 338 K (64.85° C.) overnight, calcined in air at 573 K (299.85° C.) (3 K $min^{-1}$) for 3 h, and reduced in a 10 vol % $H_2$/He flow of 20 $cm^3$ STP $min^{-1}$ at 673 K (399.85° C.) (3 K $min^{-1}$) for 4 h. These catalysts were denoted as CuFe/(K)Zx.

The MFI zeolite support when supporting the bimetallic catalyst CuFe advantageously presents a mesoporous surface area that has been moderately reduced compared to the commercial MFI zeolite support. Also, the porous volume moderately decreases.

Upon reduction, metallic copper was detected for all the catalysts (2θ=43.5° and 50.6°). Based on the Scherrer equation, the particle size of copper has been found in the range of 9 nm to 16 nm.

Table 2 indicates the data of the catalyst composition (catalyst+MFI zeolite supports) used in the present disclosure.

TABLE 2

Characterization data of the catalyst composition (catalyst + MFI zeolite supports) used in the present disclosure.

| Catalyst | Bulk Cu/Fe molar ratio$^a$ | CuFe loading$^b$ (wt. %) | $V_{pore}{}^c$ ($cm^3$ $g^{-1}$) | $S_{BET}{}^d$ ($m^2$ $g^{-1}$) | $d_{Cu}{}^e$ (nm) |
|---|---|---|---|---|---|
| CuFe/Z15 | 2.03 | 5.3 | 0.24 | 324 | 12.4 |
| CuFe/Z40 | 2.00 | 4.7 | 0.23 | 349 | 9.3 |
| CuFe/Z140 | 1.92 | 5.4 | 0.20 | 349 | 15.2 |

TABLE 2-continued

Characterization data of the catalyst composition
(catalyst + MFI zeolite supports) used in the present disclosure.

| Catalyst | Bulk Cu/Fe molar ratio[a] | CuFe loading[b] (wt. %) | $V_{pore}$[c] (cm$^3$ g$^{-1}$) | $S_{BET}$[d] (m$^2$ g$^{-1}$) | $d_{Cu}$[e] (nm) |
|---|---|---|---|---|---|
| CuFe/Z1000 | 1.99 | 5.5 | 0.16 | 288 | 15.2 |
| CuFe/HZ1000 | 2.07 | 5.2 | 0.39 | 440 | 7.6 |

[a] Determined by ICP-OES.
[b] Determined by XRF.
[c] Volume adsorbed at p/p$_0$ = 0.99.
[d] BET method.
[e] Determined from the (111) reflection of Cu in the XRD pattern using the Scherrer equation.

The H$_2$-TPR profiles of the calcined samples evidence two main peaks centred between 465-481 K and 565-587 K and have been attributed to the reduction of CuO to Cu and to the reduction of Fe$_2$O$_3$ to Fe$_3$O$_4$, respectively (see FIG. 1). The multicomponent nature of these signals suggests the presence of oxide particles of different size and location, maybe due to a combination of deposition and ion exchange upon dry impregnation. In the profile of CuFe/Z1000, the CuO reduction peak has a low-temperature shoulder, which can be attributed to the reduction of isolated CuO to Cu$_2$O. In the case of CuFe/Z15, a broad signal due to the reduction of Fe$_3$O$_4$ to Fe is evident between 673-973 K (399.85-699.85° C.), indicating a better reducibility of Fe in this sample as a consequence of a higher dispersion or a greater contact with the Cu phase that can facilitate hydrogen spillover to the iron. Still, the reducibility of the metals was quite similar in all samples in spite of the distinct acidity, except for CuFe/Z15. In view of the similarity of the H$_2$-TPR profiles of CuFe/Z40 and CuFe/Z1000, it is inferred that the finely distributed copper and iron might still be in cationic form and not substantially contribute to the reaction. Hence, the difference in selectivity patterns is mostly determined by the acidity.

Example 3: Production of Supported FeCu Catalysts Promoted with Potassium

Potassium can be added to the catalyst composition by adding a potassium precursor (e.g., K$_2$CO$_3$) to the solution of copper and iron precursors, prior to the dry impregnation onto the MFI zeolite support. More specifically, potassium was deposited onto Z1000 and Z40 simultaneously to Cu and Fe upon dry impregnation.

Alternatively, potassium can be added to the catalyst composition by ion-exchange of the MFI zeolite support. Thus, Z40 was ion-exchanged with potassium to generate a solid (KZ40), which was then impregnated with the copper and iron precursors, or with copper, iron and potassium precursors.

To produce K-promoted CuFe catalysts supported on Z1000, Z40, and KZ40, K$_2$CO$_3$ (0.59-5.9 mg, Aldrich Fine Chemicals, 98-103%) was added to the Cu- and Fe-containing solution prior to the impregnation. Bulk molar K/(Cu+Fe) ratios of 0.01 were targeted for all catalysts, while ratios of 0.005 and 0.05 were additionally considered only for Z1000-supported materials. These catalysts were denoted as KCuFe/(K)Zx-y, where y corresponds to the nominal bulk molar K/(Cu+Fe) ratio.

Table 3 indicates the data of the catalyst composition comprising potassium.

TABLE 3

Characterization data of the catalyst composition promoted with potassium used in the present disclosure.

| Catalyst | Bulk K/Cu + Fe ratio | Bulk Cu/Fe molar ratio[a] | CuFe loading[b] (wt. %) | $V_{pore}$[c] (cm$^3$ g$^{-1}$) | $S_{BET}$[d] (m$^2$ g$^{-1}$) | $d_{Cu}$[e] (nm) |
|---|---|---|---|---|---|---|
| KCuFe/Z40-0.01 | 0.009 | 2.05 | 5.2 | 0.24 | 372 | 11.2 |
| CuFe/KZ40 | 0.413 | 2.06 | 5.6 | 0.22 | 355 | 12.4 |
| KCuFe/KZ40-0.01 | 0.425 | 2.05 | 5.1 | 0.23 | 351 | 12.5 |
| KCuFe/Z1000-0.005 | 0.006 | 2.04 | 5.2 | 0.18 | 299 | 12.6 |
| KCuFe/Z1000-0.01 | 0.011 | 2.01 | 5.1 | 0.17 | 304 | — |
| KCuFe/Z1000-0.05 | 0.048 | 2.07 | 5.4 | 0.20 | 339 | 13.4 |

[a] Determined by ICP-OES.
[b] Determined by XRF.
[c] Volume adsorbed at p/p$_0$ = 0.99.
[d] BET method.
[e] Determined from the (111) reflection of Cu in the XRD pattern using the Scherrer equation.

For CuFe/KZ40, the amount of potassium measured corresponded to 96% of the total amount required to replace all protons in ion-exchange positions in Z40. Accordingly, the $C_{BAS}$ and $C_{LAS}$ for this support (6 and 9 µmolg$^{-1}$, respectively) resembled those of Z1000 (see Table 1).

Based on XRD, the presence of potassium along with Cu and Fe in the synthesis facilitated the dispersion of Cu on Z1000, Z40, and KZ40, which featured particles with a size ranging between 11 nm and 13 nm in all cases, except for KCuFe/Z1000-0.01, for which no copper reflections were identified at all. Also, for CuFe/KZ40, the copper particles had a similar particle size, which thus was moderately larger compared to the potassium-free analogue. While no reflections specific to metallic iron were detected for potassium-containing Z40- and KZ40-supported catalysts and KCuFe/Z1000-0.005, diffraction peaks of metallic iron were identified for KCuFe-Z1000-0.01 and KCuFe-Z1000-0.05

Figure 2:
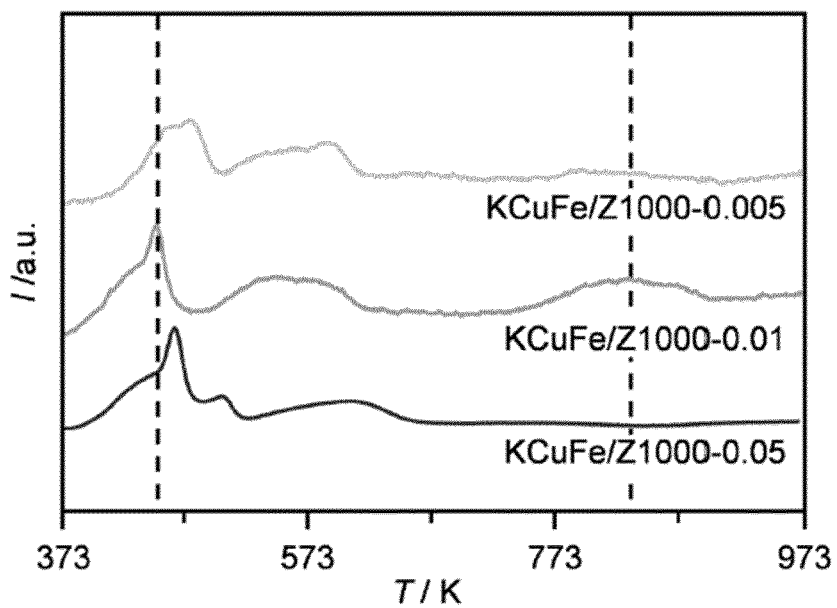
FIG. 2 shows the H$_2$-TPR profiles of the calcined CuFe catalyst supported on Z1000 and promoted by different amounts (0.005, 0.01 and 0.05) of potassium.
Figure 3:
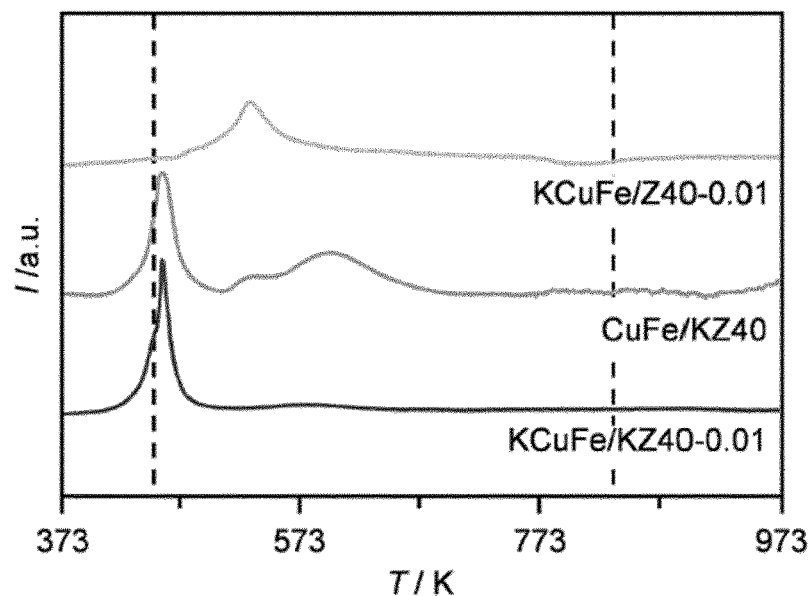
FIG. 3 shows the H$_2$-TPR profiles of the calcined CuFe catalyst supported on a zeolite with a Si/Al ratio of 40 (Z40) or potassium-exchanged Z40 and/or promoted by potassium.

Based on the H$_2$-TPR profiles collected, the copper phase was generally more reducible, as indicated by the stronger asymmetry of the CuO reduction peak, featuring a pronounced shoulder between 400-450 K (126.85-176.85° C.) in most cases (see FIGS. 2 and 3). The contribution due to the reduction of the iron phase remained in a similar temperature range for CuFe/KZ40, KCuFe/Z1000-0.005, KCuFe/Z1000-0.01, and KCuFe/Z1000-0.05, while it disappeared for KCuFe/KZ40-0.01, suggesting a more difficult Fe reduction. For KCuFe/Z1000-0.01, it was accompanied by an additional feature between 760-900 K (486.85-626.85° C.), evidencing higher reducibility of iron oxide in this catalyst, and thus implying a better contact with the more dispersed copper phase. KCuFe/KZ40-0.01 produced a distinctive curve, comprising a single peak with a maximum at 528 K (254.85° C.) with a tail reaching up to 790 K (516.85° C.), which suggests a more hindered reduction of the metals.

Example 4: Catalyst Compositions Testing for Direct Conversion of Syngas to HA The direct conversion of syngas to HA was carried out in a continuous-flow fixed-bed reactor setup. Typically, 0.5 g (sieve fraction=0.05-0.12 mm) of undiluted catalyst were loaded into the reactor and purged with an Ar (Messer, ≥99.999%) flow of 100 cm$^3$ STP min$^{-1}$ for 0.5 h at ambient pressure.

Under the same flow, the pressure was then increased to 5 MPa and a leak test was conducted.

The catalyst compositions were activated by exposing it to 10 vol % $H_2$/Ar at the same rate as previously applied at 0.5 MPa and 573 K (299.85° C.) (3 K min$^{-1}$) for 3 h. The reaction was carried out by feeding a mixture of $H_2$ (PanGas, ≥99.999%), CO (Messer, ≥99.997%), and Ar with a molar $H_2$/CO/Ar ratio of 6/3/1 at 543 K (269.85° C.) and 5 MPa. The feed flow rate was varied (WHSV=500-48000 cm$^3$ STP $g_{cat}^{-1}$ h$^{-1}$) in order to compare different systems at the same CO conversion rate (4%). The data collected represent the average value of 4-5 measurements taken between ca. 11-15 hon stream.

Testing of the Catalyst Compositions Devoid of Potassium

The catalyst compositions have been tested into the conversion of syngas to alcohols. Depending on the acidity of the catalyst, and notably of the MFI zeolite support, the selectivity to HA can be tuned. Table 4 reports the results obtained at 543 K (269.85° C.) and 5 MPa with a molar ratio $H_2$/CO of 2 and a weight hourly space velocity of 4000 cm$^3$ $g_{cat}^{-1}$ h$^{-1}$.

TABLE 4

Performance data of the CuFe catalysts supported on MFI zeolites at WHSV of 4000 cm$^3$ $g_{cat}^{-1}$ h$^{-1}$.

| Catalyst | $X_{CO}$ (%) | $S_{MeOH}$ (%) | $S_{DME}$ (%) | $S_{HA}$ (%) | $S_{1-HA}$ (%) | $S_{2-HA}$ (%) | $S_{alkanes}$ (%) | $S_{alkanes}$ (%) | $S_{CO2}$ (%) |
|---|---|---|---|---|---|---|---|---|---|
| CuFe/Z15 | 6 | 0 | 8 | 27 | 11 | 16 | 1 | 51 | 13 |
| CuFe/Z40 | 5 | 0 | 6 | 35 | 11 | 24 | 3 | 42 | 14 |
| CuFe/Z140 | 9 | 0 | 5 | 29 | 8 | 21 | 7 | 51 | 8 |
| CuFe/Z1000 | 25 | 3 | 0 | 23 | 18 | 5 | 9 | 54 | 11 |
| CuFe/HZ1000 | 22 | 8 | 1 | 17 | 15 | 2 | 9 | 53 | 12 |

The results demonstrate that the catalyst composition of the present disclosure allows for the production of HA from syngas conversion.

It has been also revealed that different selectivities can be achieved depending on the acidity of the MFI zeolite support. At high acidity, namely with a Si/Al molar ratio below 200, preferably below 140, the bimetallic catalyst CuFe deposited on the MFI zeolite can achieve at least 25% of selectivity into C2+ alcohols. No generation of methanol has been observed.

The use of zeolite obtained by desilication as heterogeneous support of a bimetallic catalyst also allows for the converting syngas into C2+ alcohols. Based on $H_2$-TPR (see FIG. 1), CuO reduction occurred at a relatively low temperature (453 K-179.85° C.), consistently with the small particle size of Cu, while the signal related to the partial reduction of $Fe_2O_3$ appeared at a comparatively higher temperature (703 K-429.85° C.), suggesting that the increased dispersion led to a more limited contact among the two metal phases. CuFe/HZ1000 displayed a very similar performance to CuFe/Z1000, attaining comparable CO conversion rate (22 versus 25%) and selectivity pattern (HA selectivity=31 versus 33%) at a CO conversion rate of 4% (see table 5), indicating that the additional porosity in the hierarchical sample was not instrumental to generate metal phases with superior properties.

The WHSV was adjusted to evaluate the product distributions at the same rate of conversion of carbon monoxide, namely at a CO conversion rate of 4% (Table 5).

TABLE 5

Performance data of the CuFe catalysts supported on MFI zeolites at CO conversion rate of 4%. WHSV is expressed in cm$^3$ $g_{cat}^{-1}$ h$^{-1}$.

| Catalyst | WHSV | $S_{MeOH}$ (%) | $S_{DME}$ (%) | $S_{HA}$ (%) | $S_{1-HA}$ (%) | $S_{2-HA}$ (%) | $S_{alkanes}$ (%) | $S_{alkanes}$ (%) | $S_{CO2}$ (%) |
|---|---|---|---|---|---|---|---|---|---|
| CuFe/Z15 | 6000 | 0 | 7 | 30 | 11 | 19 | 2 | 48 | 13 |
| CuFe/Z40 | 8000 | 0 | 5 | 35 | 12 | 23 | 6 | 41 | 13 |
| CuFe/Z140 | 14000 | 0 | 3 | 33 | 17 | 16 | 9 | 46 | 9 |
| CuFe/Z1000 | 28000 | 10 | 0 | 33 | 29 | 4 | 11 | 41 | 5 |
| CuFe/HZ1000 | 16000 | 11 | 1 | 31 | 28 | 3 | 11 | 39 | 7 |

The results of Table 5 show the importance of the WHSV in the process for syngas conversion into C2+ alcohols. It has thus been possible to achieve a selectivity comprised between 30% and 35% with the catalyst composition of the present disclosure, namely with a bimetallic catalyst CuFe having a CuFe molar ratio superior to 1 and deposited on an MFI zeolite support.

Figure 4:
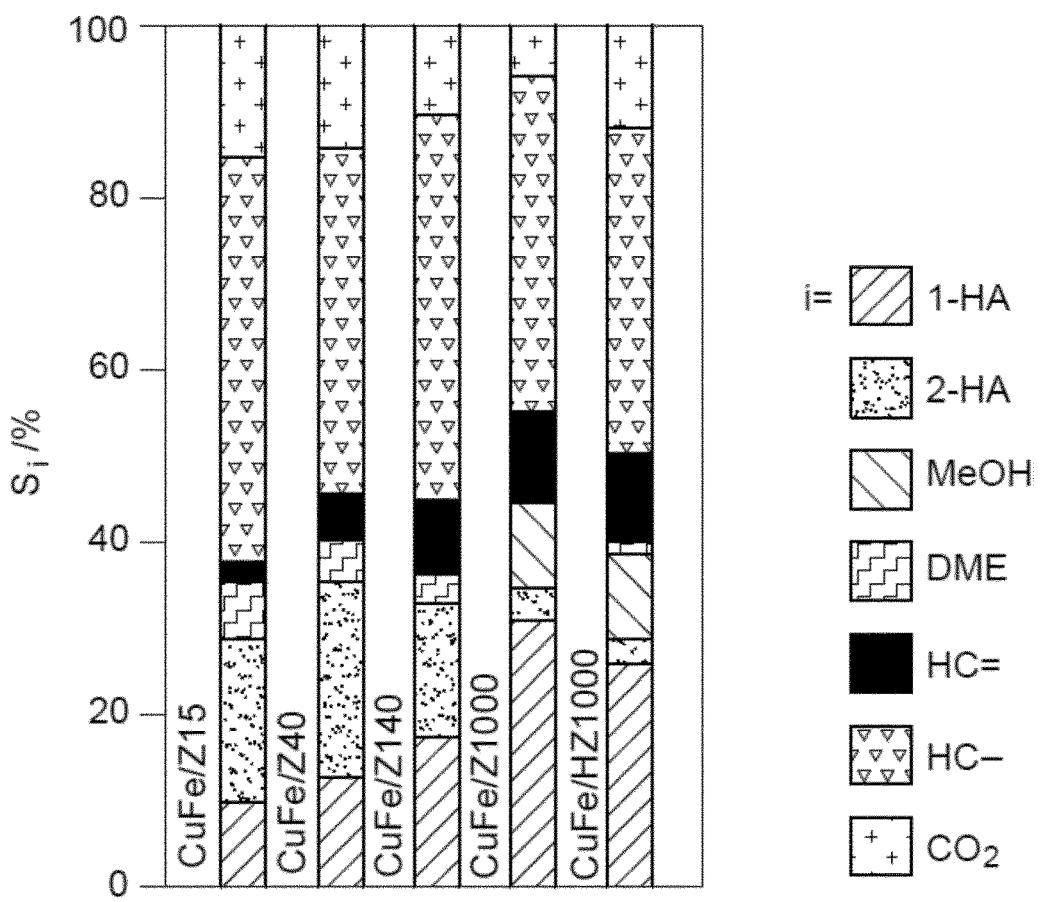
FIG. 4 shows the selectivity to the different product at a CO conversion rate of 4% over CuFe catalyst supported on MFI zeolites with different Si/Al molar ratio and porosity.

FIG. 4 shows the selectivities obtained with the catalyst composition of the present disclosure in the process for converting syngas into C2+ alcohols at a CO conversion rate of 4%. The C2+ alcohols selectivity fell in a narrow range (30-35%), but the amount of 2-HA increased at the expense of 1-HA over more acidic materials. All catalysts reached a steady performance after 2-3 h on stream and no deactivation was observed during the remainder of the run (up to 15 h). In line with this, thermogravimetric analysis (TGA) of used CuFe/Z40 confirmed the absence of substantial coke deposits (4% mass loss only).

The fraction of 2-HA within HA was as low as 10% over CuFe/HZ1000 and reached up to 63% over CuFe/Z15.

For all materials, hydrocarbons predominantly comprised alkanes, the selectivity of which increased with the Al content (up to 48%).

The alkenes selectivity had an opposite dependence on the support acidity, dropping from 11% over CuFe/Z100 to 2% over CuFe/Z15.

Methanol was only produced on CuFe/Z1000, whereas higher Al contents facilitated dimethyl ether (DME) formation (selectivity=7% over CuFe/Z15).

The $CO_2$ selectivity increased from 5% over CuFe/Z1000 to 13% over CuFe/Z15.

Figure 5:
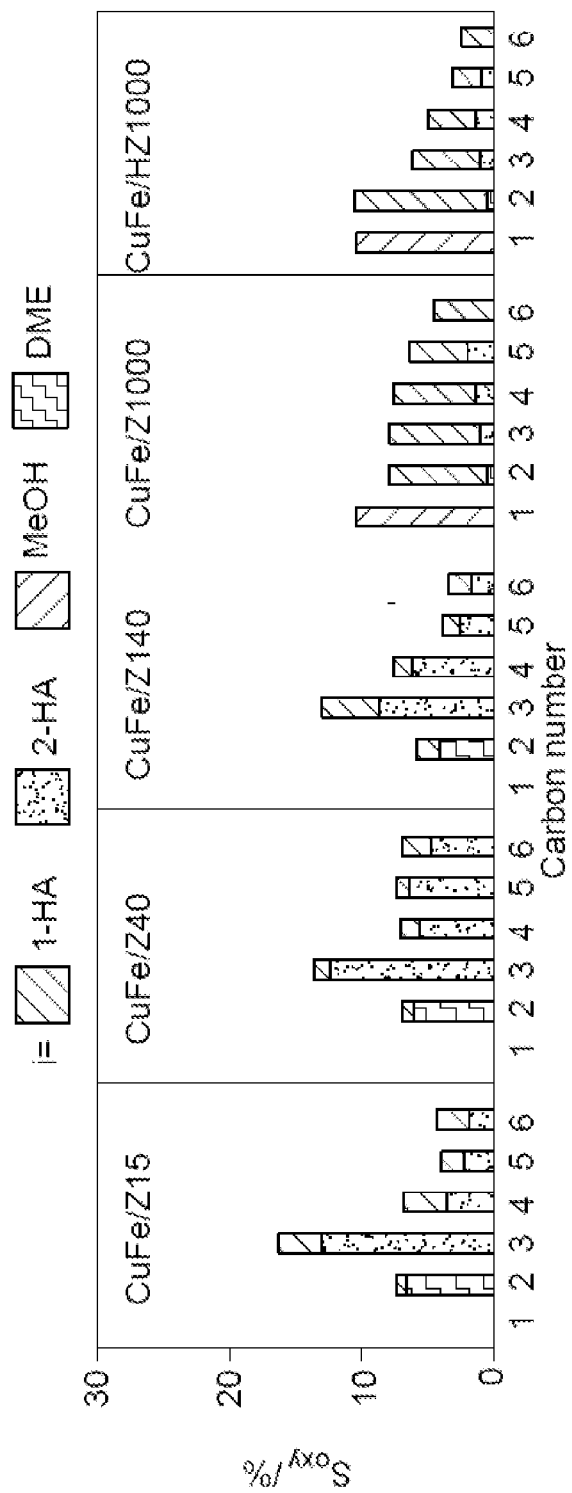
FIG. 5 shows the distribution of oxygenates versus carbon number in the chain at a CO conversion rate of 4% with CuFe catalyst supported on MFI zeolites with different Si/Al molar ratio and porosity.

A closer analysis of the selectivities towards oxygenates and hydrocarbons for distinct chain lengths (FIG. 5) evidenced that the formation of propanols (C3 alcohols), mainly 2-propanol, was boosted in the presence of Z140, Z40, and Z15 while that of ethanol (C2 alcohol) was dramatically suppressed and that of heavier alcohols dropped consistently.

Figure 6:
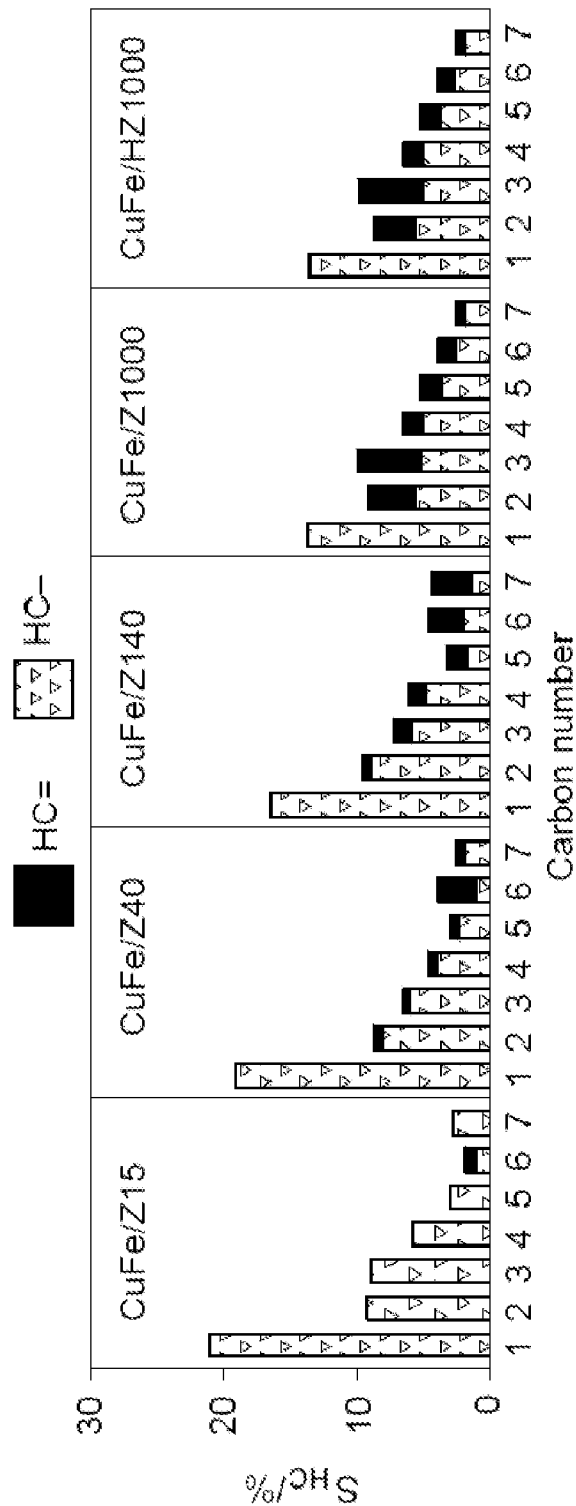
FIG. 6 shows the distribution of hydrocarbons versus carbon number in the chain at a CO conversion rate of 4% with CuFe catalyst supported on MFI zeolites with different Si/Al molar ratio and porosity.

Regarding hydrocarbons (FIG. 6), the methane selectivity was fostered over the catalysts with Al-rich supports, which produced less propane/propene, namely over the catalyst presenting an acidic MFI zeolite support. The increase of the methane selectivity at the expenses of that to ethanol hinted that CO insertion was hindered.

Selectivity in Function of Acidity of the MFI Zeolite Support

Figure 7:
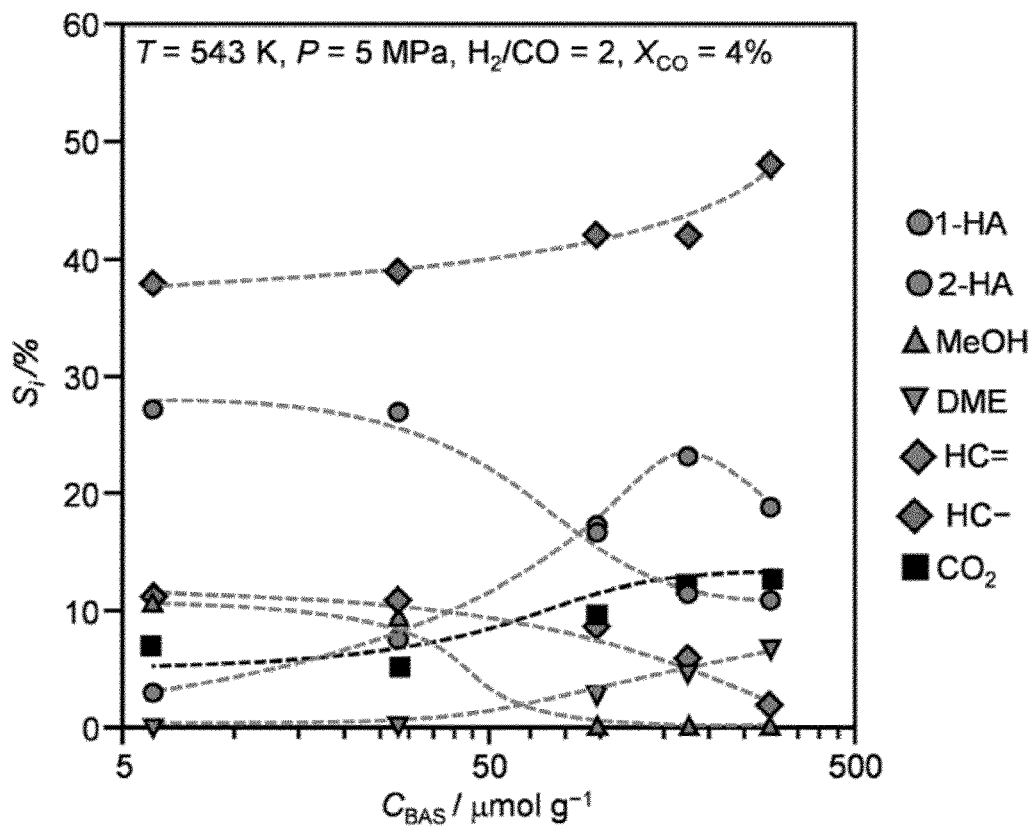
FIG. 7 shows the selectivity to the products versus the density of Brønsted-acid sites ($C_{BAS}$) of the MFI zeolite supports for the CuFe bimetallic catalysts supported on MFI zeolites with different Si/Al molar ratio and porosity.

The selectivity to the different products was plotted against the density of Brønsted-acid sites in FIG. 7. The conversion of syngas was conducted at 543 K (269.85° C.), at 5.0 MPa and with a molar ratio $H_2$/CO of 2.

It indicates that the formation of 1-HA, methanol and alkenes was suppressed when the density of Brønsted-acid sites increases, while the generation of $CO_2$ and alkanes was increased. Also, upon an increase of acidity, a volcano relation was observed for the production of 2-HA. The shifts in product distribution can be explained as follows:

(i) 2-HA are likely formed from alkenes through acid-catalyzed hydration. Indeed, acids such as $H_2SO_4$ and $H_3PO_4$ were reported to mediate this reaction and bare zeolites of different topologies (i.e., MOR, MFI, FER, USY) were also examined for the transformation of ethylene or propylene to their respective 2-HA through water co-feeding.

(ii) DME production is speculated to be due to methanol dehydration over the acid sites. The decrease in DME selectivity at higher WHSV corroborates that it is a secondary reaction.

(iii) The high alkanes and, especially, methane selectivity indicate that adsorbed carbon species undergo hydrogenation and coupling and these reactions are more easily followed by acid-catalyzed consecutive reactions rather than CO and CHO insertion to form HA. In other words, insertion of CO or CHO is suppressed due to acidic zeolite supports.

This implies that Fe works well as a Fischer-Tropsch catalyst, but the action of Cu of providing molecularly activated CO is hindered.

Testing of the Catalyst Comprising Potassium

Introduction of potassium, either as a promoter of the bimetallic catalyst CuFe or as the cation of the MFI zeolite support allows for tuning the selectivity. Table 6 shows the results of the introduction of the potassium onto acidic support (Z40) and less acidic support (Z1000).

TABLE 6

Performance data of the CuFe catalysts supported on MFI zeolites at WHSV of 4000 $cm^3$ $g_{cat}^{-1}$ $h^{-1}$ and comprising potassium.

| Catalyst | $X_{CO}$ (%) | $S_{MeOH}$ (%) | $S_{DME}$ (%) | $S_{HA}$ (%) | $S_{1-HA}$ (%) | $S_{2-HA}$ (%) | $S_{alkanes}$ (%) | $S_{alkanes}$ (%) | $S_{CO2}$ (%) |
|---|---|---|---|---|---|---|---|---|---|
| CuFe/KZ40 | 17 | 4 | 2 | 29 | 25 | 4 | 9 | 44 | 12 |
| KCuFe/Z40-0.01 | 4 | 0 | 7 | 40 | 12 | 28 | 6 | 41 | 6 |
| KCuFe/KZ40-0.01 | 21 | 11 | 0 | 21 | 18 | 3 | 4 | 52 | 12 |
| KCuFe/Z1000-0.005 | 18 | 3 | 1 | 28 | 24 | 4 | 12 | 51 | 5 |
| KCuFe/Z1000-0.01 | 23 | 2 | 1 | 30 | 22 | 8 | 6 | 49 | 12 |
| KCuFe/Z1000-0.05 | 48 | 4 | 0 | 12 | 11 | 1 | 2 | 48 | 34 |

Introduction the potassium as the cation of the MFI zeolite has led to a decrease of selectivity of C2+ alcohol from 35% to 29%. However, the introduction of the potassium as a promotor of the bimetallic catalyst CuFe in a molar ratio K(Cu+Fe) of 0.01 has led to an increase of selectivity into C2+ alcohols from 35% to 40% when using an acidic MFI zeolite as support.

The use of potassium as the cation of the MFI zeolite, even if the bimetallic catalyst CuFe is promoted with potassium, provides a decrease of selectivity.

Starting with less acidic support (Z1000), the promotion of the bimetallic catalyst CuFe with potassium leads to an increase of selectivity into C2+ alcohols when the potassium is in a molar ratio K(Cu+Fe) inferior to 0.05.

Testing in the direct hydrogenation of CO at 543 K (269.85° C.), 5 MPa, and 4000 $cm^3$ $g_{cat}^{-1}$ $h^{-1}$ indicated that the potassium-containing catalysts reached distinct activity levels. KCuFe/Z40-0.01 attained essentially the same CO conversion rate as CuFe/Z40 (4 versus 5%), while CuFe/KZ40 and KCuFe/KZ40 reached higher values (17 and 21%, respectively). The addition of a smallest amount of K to CuFe/Z1000 resulted in a slight drop in CO conversion rate compared to the potassium-free catalyst (18 versus 25% in CuFe/Z1000-0.005), while the highest K loading doubled the activity (CO conversion rate=48%, CuFe/Z1000-0.05).

The WHSV was adjusted to evaluate the product distributions at the same level of conversion of carbon monoxide, namely at a CO conversion rate of 4% (Table 7). A reference catalyst, namely a bimetallic CuFe promoted with potassium and supported on carbon nanofibers instead of MFI zeolite was used as a comparison point.

TABLE 7

Performance data of the CuFe catalysts supported on MFI zeolites at CO conversion rate of 4%. WHSV is expressed into $cm^3$ $g_{cat}^{-1}$ $h^{-1}$.

| Catalyst | WHSV | $S_{MeOH}$ (%) | $S_{DME}$ (%) | $S_{HA}$ (%) | $S_{1-HA}$ (%) | $S_{2-HA}$ (%) | $S_{alkanes}$ (%) | $S_{alkanes}$ (%) | $S_{CO2}$ (%) |
|---|---|---|---|---|---|---|---|---|---|
| KCuFe/Z40-0.01 | 24000 | 0 | 7 | 40 | 12 | 28 | 6 | 41 | 6 |
| CuFe/KZ40 | 24000 | 10 | 0 | 39 | 35 | 4 | 11 | 34 | 6 |
| KCuFe/KZ40-0.01 | 28000 | 13 | 0 | 31 | 27 | 4 | 10 | 42 | 4 |
| KCuFe/Z1000-0.005 | 32000 | 11 | 0 | 41 | 37 | 4 | 11 | 33 | 4 |
| KCuFe/Z1000-0.01 | 34000 | 7 | 0 | 43 | 38 | 5 | 11 | 37 | 2 |
| KCuFe/Z1000-0.05 | 32000 | 7 | 0 | 20 | 19 | 1 | 12 | 36 | 25 |
| Reference catalyst | 34000 | 10 | 0 | 38 | 35 | 3 | 20 | 19 | 13 |

The results of table 4 indicate that at least 31% of conversion into C2+ alcohols is achieved with the catalyst of the present disclosure, except when the amount of the potassium loading reaches 0.05.

By comparison with the reference catalyst, having a carbonaceous support (for instance, carbon nanofibers or conical carbon nanofibers), introduction of potassium onto acidic MFI zeolite support (Z40) either as cation of said MFI zeolite or as a promotor of the bimetallic catalyst CuFe; or introduction of potassium onto less acidic MFI zeolite support (Z1000) as promotor of bimetallic catalyst CuFe, have allowed for achieving selectivity into C2+ alcohols superior to what was achieved in the prior art, namely a selectivity of 38% at 4% conversion of carbon monoxide. It is further remarkable that the best catalyst composition of the present disclosure generates only 2% of $CO_2$ (compared to 13% of $CO_2$ generated by the reference catalyst at the same 4% conversion of carbon monoxide).

Figure 8:
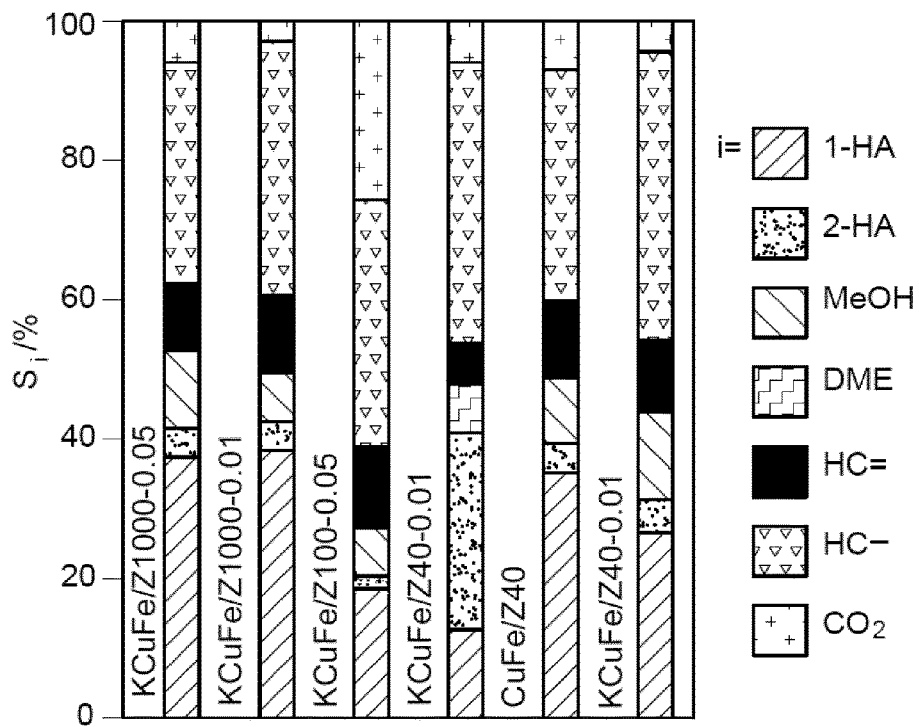
FIG. 8 shows the selectivity to the different product at a CO conversion rate of 4% over CuFe catalyst promoted with potassium and supported on MFI zeolites with different Si/Al molar ratio and porosity.

FIG. 8 shows the selectivities obtained with the catalyst composition of the present disclosure promoted with potassium in the process for converting syngas into C2+ alcohols at a CO conversion rate of 4%.

As expected, based on a similar support acidity, the performance of CuFe/KZ40 was comparable to that of CuFe/Z1000, indicating that potassium in exchange position does not affect the action of Cu and Fe. Addition of potassium upon deposition of CuFe onto the Z40 led to minor improvements compared to CuFe/Z40, slightly enhancing the already high 2-HA selectivity and halving the $CO_2$ selectivity. Depositing potassium along with Cu and Fe on potassium-exchanged Z40 produced almost no effect, in striking contrast to the addition of the same amount of K to the acidity-wise analogue CuFe/Z1000.

When comparing KCuFe/Z1000-0.005 with its corresponding potassium-free solid, the HA selectivity was enhanced from 33 to 41% chiefly at the expense of alkanes, the selectivity of which was suppressed from 40 to 32%. At a K/(Cu+Fe) ratio of 0.01, the HA selectivity reached 43%.

While alkanes were formed to an only slightly inferior extent, the production of methanol and $CO_2$ was more hindered. The latter reached a record value of 2% over this sample. At a higher potassium loading (ratio 0.05), the methanol and HA selectivities substantially dropped (to 7 and 20%, respectively).

Compared to the reference catalyst, KCuFe/Z1000-0.01 displayed a higher HA selectivity (43 versus 38%) and formed less methanol (7 versus 10%) and especially $CO_2$ (2 versus 13%), but generated a greater fraction of alkanes than alkenes.

Figure 9:
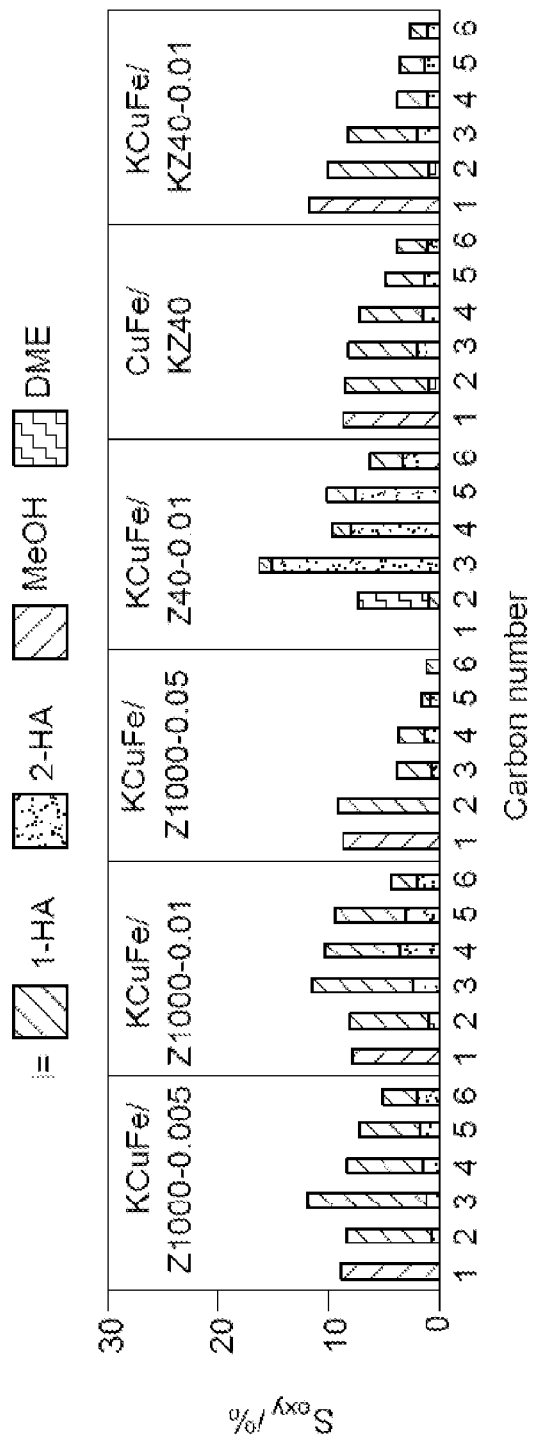
FIG. 9 shows the distribution of oxygenates versus carbon number in the chain at a CO conversion rate of 4% with a CuFe catalyst promoted with potassium and supported on MFI zeolites with different Si/Al molar ratio and porosity.

A closer analysis of the selectivities towards oxygenates for distinct chain length (see FIG. 9) evidenced that the formation of propanols (C2+ alcohols), mainly 1-propanol, was boosted in the presence of the bimetallic catalyst CuFe deposited on an MFI zeolite support having a Si/Al molar ratio of 1000. Using a potassium-exchange MFI zeolite leads to similar results. Using a more acidic support, namely, an MFI zeolite Z40 turns the selectivity essentially toward 2-HA, mainly 2-propanol.

Figure 10:
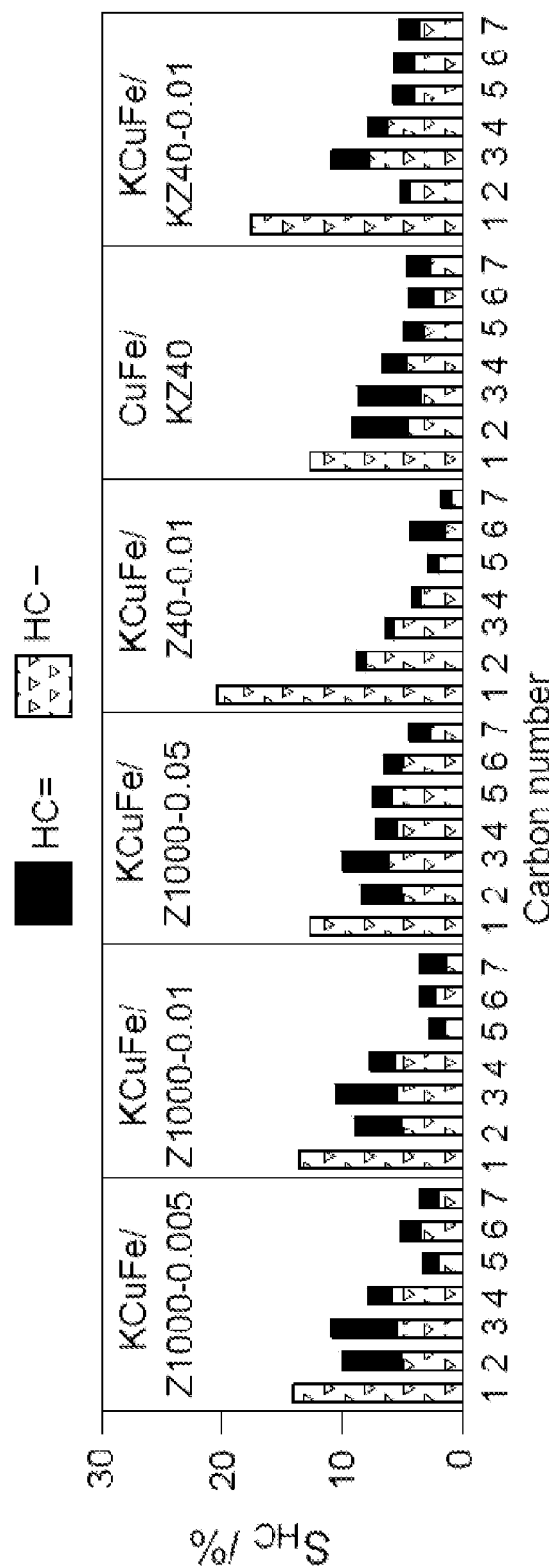
FIG. 10 shows the distribution of hydrocarbons versus carbon number in the chain at a CO conversion rate of 4% with a CuFe catalyst promoted with potassium and supported on MFI zeolites with different Si/Al molar ratio and porosity.

With regard to the hydrocarbon selectivities (see FIG. 10), the methane selectivity was fostered over the catalyst with Al-rich supports, as it was the case for catalyst devoid of potassium.

Mechanistic Studies: Acid-Catalyzed Conversion of the Main Product Types.

In order to determine the mechanism of the reaction, the different products generated from the conversion of syngas into C2+ alcohols were converted over an acidic MFI zeolite.

Specifically, (i) a first fraction of 1-HA (i.e. C2+ primary alcohol), namely ethanol/propan-1-ol/butan-1-ol/water in a 1/1/1/2 molar ratio, (ii) a second fraction of 2-HA (i.e. C2+ secondary alcohol), namely propan-2-ol/butan-2-ol/water in a 1/1/2.5 molar ratio, (iii) a third fraction of C3+ hydrocarbons, namely propane/prop-1-ene/butane/but-1-ene/water in a 1/1/1/1/3.5 molar ratio, and/or, optionally (iv) a fourth fraction of methanol were introduced in argon along with water over Z40 at 543 K (269.85° C.) and at 5.0 MPa, with a WHSV of 8000 $cm^3$ $g_{cat}^{-1}$ $h^{-1}$.

Figure 11:
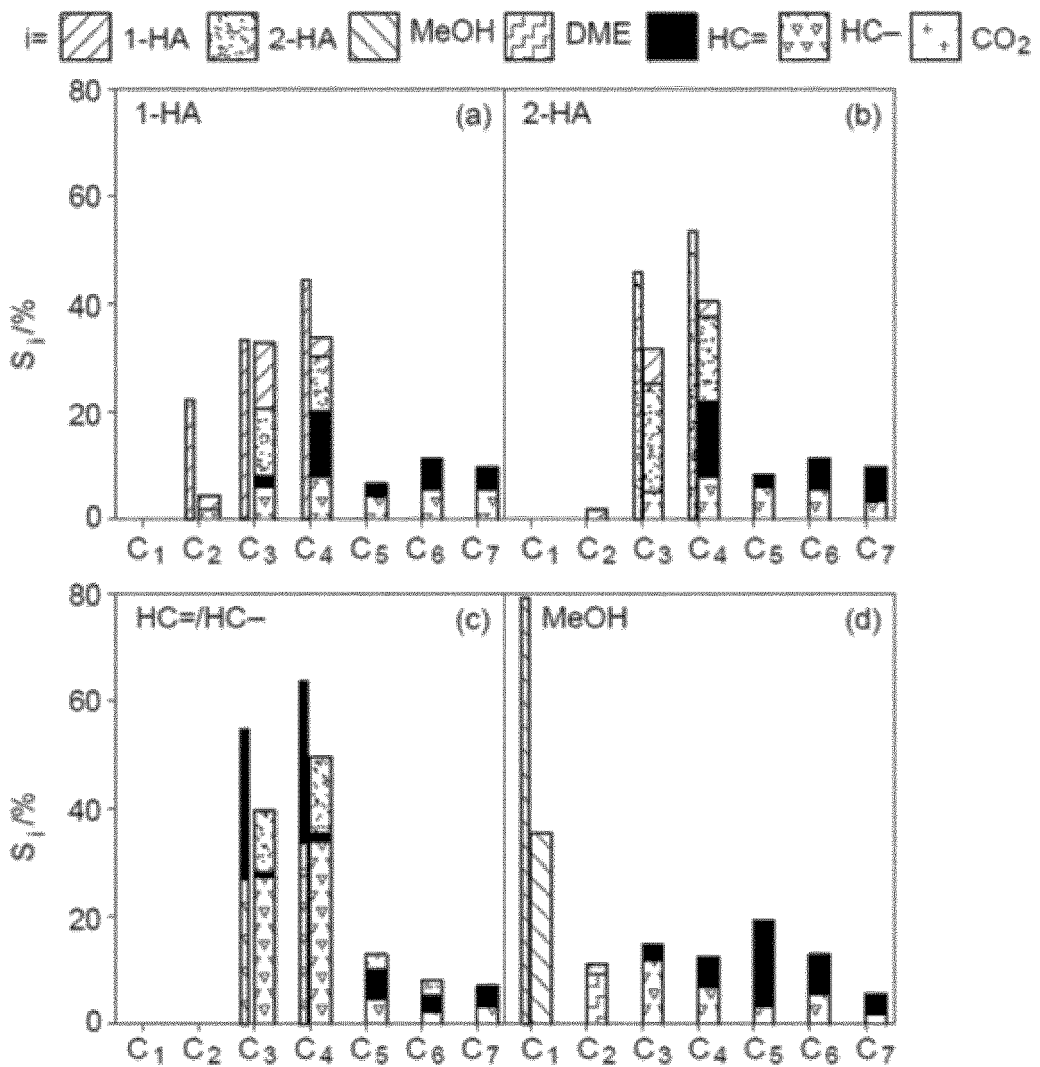
FIG. 11 shows the distribution of the products when (a) a first fraction comprising primary alcohols (1-HA) is hydrated, (b) a second fraction comprising secondary alcohols (2-HA) is hydrated, (c) a third fraction comprising C3+ hydrocarbons is hydrated and (d) a fourth fraction comprising methanol is hydrated on MFI zeolite.

FIG. 11*a* shows the results for the conversion of the first fraction. More than 80% of ethanol and butan-1-ol and 60% of propan-1-ol were transformed. Ethanol primarily generated heavier compounds (C3-C7) and a small amount of ethane. The produced C3 compounds mainly comprised 2-HA, a considerable amount of alkanes, and a minor fraction of alkenes. Within the C4 species, alkenes were the main constituents, followed by 2-HA and alkanes. C5-C7 alkanes and alkenes were produced to a similar extent and essentially had comparable selectivities to propane and butane. These results hinted that 1-HA dehydration to alkenes occurs, followed by either rehydration to 2-HA or coupling and cracking.

FIG. 11*b* shows the results for the conversion of the second fraction. When feeding propan-2-ol and butan-2-ol, less than half of each was converted. C3 products included propane and propan-1-ol in similar quantity and a trace amount of propylene. In the C4 fraction, a substantial quantity of but-2-ene was observed as a consequence of butan-2-ol dehydration. Butane and butan-1-ol were present in minor amounts. The formation of 1-HA indicated that alkenes could be partially hydrated at the primary carbon even if this chemoselectivity is electronically unfavored. C5-C7 species comprised similar amounts of alkanes and alkenes. The same product distributions were determined when the different mixtures of compounds were fed under a syngas environment, substantiating that the zeolites alone are inactive in CO hydrogenation.

The results for the third fraction are shown in FIG. 11*c* indicates that the propane and butane remained unaltered, while alkenes underwent a nearly full conversion into 2-HA. Approximately half of the alkenes transformed into their corresponding 2-HA via hydration and half converted into C5-C7 alkenes and alkanes through coupling, partially followed by cracking.

When methanol was fed, 55% of this alcohol was converted into C3-C7 hydrocarbons with selectivities decreasing with the carbon number, DME, and a small quantity of ethanol (see FIG. 11*d*). Alkenes mainly contributed to the hydrocarbons, with pentene being the dominant alkene.

These experiments corroborated the hydration of alkenes to 2-HA and the dehydration of methanol to DME, and highlighted the occurrence of coupling and cracking reactions leading to heavier hydrocarbons as well as the rehydration of alkenes to 1-HA. The production of $C_3$-$C_7$ alkenes and alkanes explains the gap between DME formation and methanol consumption observed over CuFe catalysts supported on Z140, Z40, and Z15 (see FIGS. 5 and 6). It also justifies the shift in alcohols distribution towards higher molecular weight compounds, since part of the longer alkenes could be further converted into 2-HA. In addition, the conversion of 1-HA into alkanes agreed with the observed decrease in 1-HA selectivity upon rising the support acidity. The chemical inertness of alkanes makes them the terminal products over Z40 and rationalizes their overall high selectivities. The types of chemical reactions involved in this network confirm the retention of a considerable fraction of Brønsted-acid sites of the support after metal deposition and activation.

Aiming at supporting the intrinsic Fischer-Tropsch and methanol syntheses activities of iron and copper and uncovering additional possible functions, attempts to prepare catalysts containing the two metals separately were conducted. In spite of the well-reproduced particle size, the Cu catalyst surprisingly was barely active. So was the Fe catalyst. In this case, it was put forward insufficient reduction due to the missing assistance of Cu as the likely reason. Reduction at higher temperature was not helpful since the iron phase sintered to an excessive extent. Even if not experimentally substantiated, it was envisaged that the metals will facilitate the hydrogenation of alkenes obtained as primary by-products and through coupling, further increasing the alkanes selectivity. These findings also indirectly substantiate the good interaction of copper and iron in the bimetallic catalyst.

Figure 12:
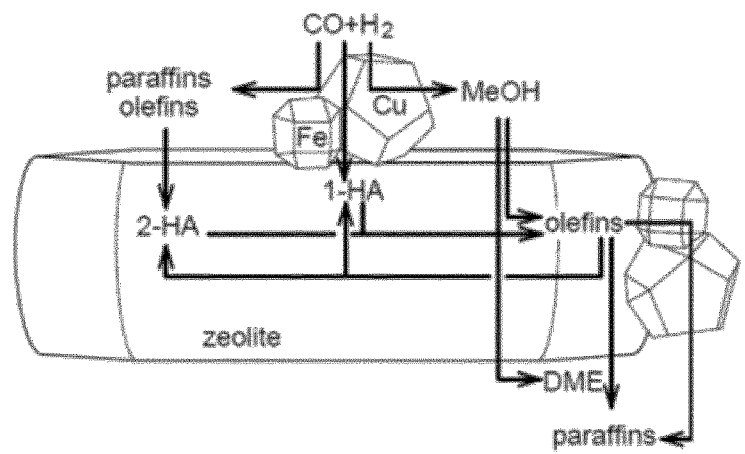
FIG. 12 shows the reaction network for the conversion of syngas to C2+ alcohols over bimetallic CuFe catalyst supported on acidic MFI zeolites.

The interplay of reactions occurring over CuFe/Z40 is summarized in FIG. 12. It is shown that the formation of alkenes is not a problem anymore since they can be hydrated into 2-HA, enhancing subsequently the selectivity of C2+ alcohols.

The invention claimed is:

1. A catalyst composition comprising an active phase comprising copper and iron on a support for use in a process for the synthesis of higher alcohols from a syngas feed stream comprising hydrogen and carbon monoxide, the catalyst composition being characterized in that the support is one or more zeolites having a Si/Al molar ratio ranging from 10 to 200 as determined by inductively coupled plasma optical emission spectroscopy (ICP-OES), in that the total content of iron and copper is ranging from 3.0 to 10 wt. % based on the total weight of the catalyst composition and as determined by X-ray fluorescence spectroscopy, in that the Cu/Fe bulk molar ratio is ranging from 1.1:1.0 to 5.0:1.0 as determined by X-ray fluorescence spectroscopy and, wherein said catalyst composition is a reduced catalyst composition as determined by X-ray diffraction, wherein the catalyst composition is devoid of iron oxide wherein iron oxide is $Fe_2O_3$, and wherein the total content of iron and copper of the catalyst composition ranges of the from 3.0 to 8.0 wt. % based on the total weight of the catalyst composition and as determined by X-ray fluorescence spectroscopy.

2. The catalyst composition according to claim 1, characterized in that the one or more zeolites are selected from MFI, FAU, MOR, FER, BEA, TON, MTT, OFF families, or any mixture thereof.

3. The catalyst composition according to claim 1, characterized in that the one or more zeolites are or comprises ZSM-5.

4. The catalyst composition according to claim 1, characterized in that said catalyst composition includes one or more zeolites having a pore volume ranging between 0.15 $cm^3 g^{-1}$ and 1.00 $cm^3 g^{-1}$, as determined by nitrogen adsorption measurement.

5. The catalyst composition according to claim 1, characterized in that the one or more zeolites have a Si/Al molar ratio ranging from 11 to 190 as determined by inductively coupled plasma optical emission spectroscopy (ICP-OES).

6. The catalyst composition according to claim 1, characterized in that the one or more zeolites have a density of Brønsted acid sites ranging from 5 $\mu mol\ g^{-1}$ to 500 $\mu mol\ g^{-1}$ as determined by Fourier transform infrared spectroscopy of adsorbed pyridine.

7. The catalyst composition according to claim 1, characterized in that the catalyst composition further comprises at least one promoter.

8. The catalyst composition according to claim 7, characterised in that the bulk molar ratio of said at least one promoter to the total content of the copper and iron is ranging from 0.001/1 to 0.5/1 as determined by inductively coupled plasma optical emission spectroscopy.

9. The catalyst composition to claim 1, characterized in that Cu/Fe bulk molar ratio is ranging from 1.2/1.0 to 4.0/1.0.

10. The catalyst composition according to claim 1, characterized in that the one or more zeolites have a mesoporous surface area comprised between 10 $m^2 g^{-1}$ and 600 $m^2 g^{-1}$ as determined by Brunauer-Emmett-Teller (BET) method.

11. The catalyst composition according to claim 1, characterized in that the Cu particle size is at least 7 nm as determined from the (111) reflection in an X-ray diffraction pattern using the Scherrer equation; and/or the Cu particle size is at most 35 nm as determined from the (111) reflection in an X-ray diffraction pattern using the Scherrer equation.

12. A method to produce a catalyst composition according to claim 1 characterised in that the method comprises the following steps:
   i. Dry impregnation of the copper and iron, and optionally at least one promoter, on the support being one or more zeolites to obtain a catalyst composition;
   ii. Optionally calcining the catalyst composition to obtain a calcined catalyst;
   iii. Activating the catalyst composition through a reduction to obtain a reduced catalyst composition.

13. A process for the synthesis of higher alcohols from a syngas feed stream comprising hydrogen and carbon monoxide, characterized in that the process comprises the following steps:
   a) Providing a syngas feed stream comprising hydrogen and carbon monoxide;
   b) Providing a catalyst composition according to claim 1;
   c) Putting the syngas feed stream in contact with the catalyst composition at a reaction pressure ranging from 1 to 10 MPa and a reaction temperature ranging from 443 K (169.85° C.) to 653 K (379.85° C.); and
   d) Recovering the effluent containing higher alcohols.

* * * * *